(12) United States Patent  
Winterberg et al.

(10) Patent No.: US 8,940,951 B2  
(45) Date of Patent: Jan. 27, 2015

(54) PREPARATION OF ISOBUTENE BY DISSOCIATION OF MTBE

(75) Inventors: Markus Winterberg, Datteln (DE); Dirk Roettger, Cologne (DE); Armin Rix, Marl (DE); Reiner Bukohl, Marl (DE); Walter Luh, Marl (DE); Holger Wiederhold, Darmstadt (DE); Gunnar Schilling, Herten (DE); Christian Boeing, Cologne (DE)

(73) Assignee: Evonik Degussa GmbH, Essen (DE)

( * ) Notice: Subject to any disclaimer, the term of this patent is extended or adjusted under 35 U.S.C. 154(b) by 67 days.

(21) Appl. No.: 13/381,680

(22) PCT Filed: Jun. 16, 2010

(86) PCT No.: PCT/EP2010/058424  
§ 371 (c)(1), (2), (4) Date: Feb. 14, 2012

(87) PCT Pub. No.: WO2011/000696  
PCT Pub. Date: Jan. 6, 2011

(65) Prior Publication Data  
US 2012/0142985 A1 Jun. 7, 2012

(30) Foreign Application Priority Data  
Jul. 1, 2009 (DE) .......................... 10 2009 027 404

(51) Int. Cl.  
*C07C 1/20* (2006.01)  
*C07C 11/09* (2006.01)

(52) U.S. Cl.  
CPC .. *C07C 11/09* (2013.01); *C07C 1/20* (2013.01)  
USPC ........... 585/324; 585/327; 585/638; 585/639; 585/648; 585/649

(58) Field of Classification Search  
USPC .......................... 585/324, 638, 639, 648, 649  
See application file for complete search history.

(56) References Cited

U.S. PATENT DOCUMENTS 4,232,177 A  11/1980  Smith  
4,242,530 A  12/1980  Smith, Jr.  
(Continued)

FOREIGN PATENT DOCUMENTS

CN  101134705 A  3/2008  
FR  2 424 502  11/1979  
(Continued)

OTHER PUBLICATIONS

Luyben, William L., Principles and Case Studies of Simultaneous Design, Chapter 3—Principles of Distillation Design and Control, 2011, Wiley & Sons Inc., p. 31-39.*

(Continued)

*Primary Examiner* — In Suk Bullock  
*Assistant Examiner* — Philip Louie  
(74) *Attorney, Agent, or Firm* — Oblon, Spivak, McClelland, Maier & Neustadt, L.L.P.

(57) ABSTRACT

A process for preparing isobutene by dissociation of MTBE, including: a) reaction of isobutene-containing hydrocarbon mixtures, with methanol, present in one or more methanol-containing streams, over acidic ion exchangers to give a stream, containing MTBE and TBA; b) separation of a stream containing MTBE and TBA, from a stream by distillation; c) dissociation of a stream in the gas phase over a heterogeneous catalyst to give a stream containing at least isobutene, methanol, MTBE and water and possibly TBA, d) separation of a stream by distillation to give a stream containing in each case more than 50% by mass of the amounts of methanol, TBA and water present in another stream and a stream containing isobutene, e) separation of water from stream to below 1% by mass by distillation to give a stream, f) total or partial recirculation of the methanol-containing stream.

18 Claims, 9 Drawing Sheets

Overall process with the individual process steps

(56) References Cited

U.S. PATENT DOCUMENTS

| | | | |
|---|---|---|---|
| 4,298,058 | A | 11/1981 | Wochele |
| 4,570,026 | A * | 2/1986 | Keyworth et al. ............ 585/312 |
| 4,925,989 | A * | 5/1990 | Hagan et al. .................. 568/697 |
| 6,657,090 | B2 | 12/2003 | Rix et al. |
| 7,361,714 | B2 | 4/2008 | Grass et al. |
| 7,473,812 | B2 | 1/2009 | Peters et al. |
| 7,737,318 | B2 | 6/2010 | Santiago-Fernandez et al. |
| 7,910,786 | B2 | 3/2011 | Winterberg et al. |
| 7,919,662 | B2 | 4/2011 | Winterberg et al. |
| 7,932,428 | B2 | 4/2011 | Rix et al. |
| 7,968,758 | B2 | 6/2011 | Winterberg et al. |
| 7,977,523 | B2 | 7/2011 | Zanthoff et al. |
| 2006/0041167 | A1 | 2/2006 | Grass et al. |
| 2006/0135833 | A1 | 6/2006 | Malzkorn et al. |
| 2007/0203369 | A1 | 8/2007 | Praefke et al. |
| 2008/0058572 | A1 | 3/2008 | Fernandez et al. |
| 2008/0058575 | A1 * | 3/2008 | Winterberg et al. .......... 585/703 |
| 2010/0081562 | A1 | 4/2010 | Lansink Rotgerink |
| 2010/0144998 | A1 | 6/2010 | Santiago-Fernandez et al. |
| 2011/0118523 | A1 | 5/2011 | Winterberg et al. |
| 2011/0152596 | A1 | 6/2011 | Zanthoff et al. |
| 2011/0217552 | A1 | 9/2011 | Schulze-Isfort et al. |

FOREIGN PATENT DOCUMENTS

| | | |
|---|---|---|
| JP | 52-151103 A | 12/1977 |
| JP | 53-112803 A | 10/1978 |
| JP | 2008-56673 A | 3/2008 |
| JP | 2008-56674 A | 3/2008 |
| JP | 2008-524271 A | 7/2008 |
| WO | 2004 018393 | 3/2004 |

OTHER PUBLICATIONS

RS Means, Environmental Remediation Estimating Methods, Chapter 26—Neutralization, 2003, Wiley & Sons Inc., p. 223-228.*
International Search Report Issued Apr. 20, 2011 in PCT/EP10/058424 Filed Jun. 16, 2010.
U.S. Appl. No. 13/381,676, filed Dec. 30, 2011, Boeing, et al.
U.S. Appl. No. 13/394,827, filed Mar. 8, 2012, Boeing, et al.
U.S. Appl. No. 13/880,862, filed Apr. 22, 2013, Winterberg, et al.
U.S. Appl. No. 13/997,677, filed Jun. 25, 2013, Schulze-Isfort, et al.
U.S. Appl. No. 14/005,479, filed Sep. 16, 2013, Winterberg, et al.
U.S. Appl. No. 13/808,010, filed Mar. 15, 2013, Boeing, et al.
Office Action issued Apr. 21, 2014 in Japanese Patent Application No. 2012-518862 (with English language translation).
Combined Chinese Office Action and Search Report issued May 8, 2014 in Patent Application No. 201010220989.9 (submitting English translation only).

* cited by examiner

Figure 1: Overall process with the individual process steps
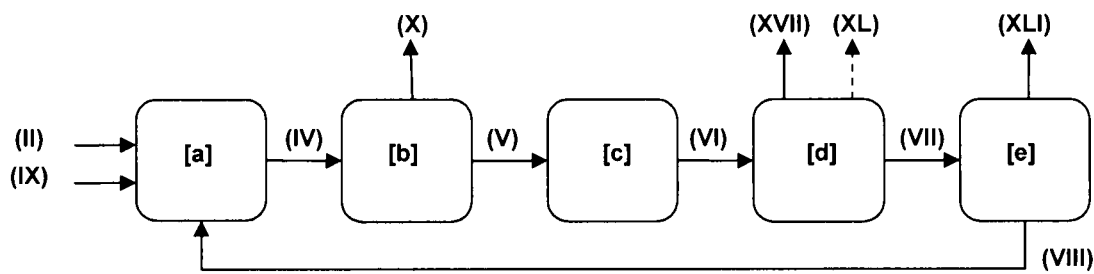
Figure 2: MTBE synthesis, preferred embodiment [a1]
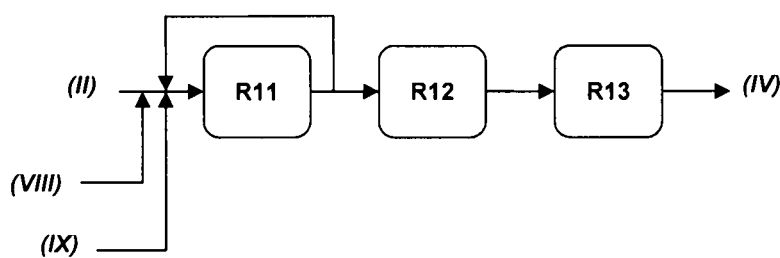

Figure 3: Isolation of MTBE, preferred embodiment [b1]
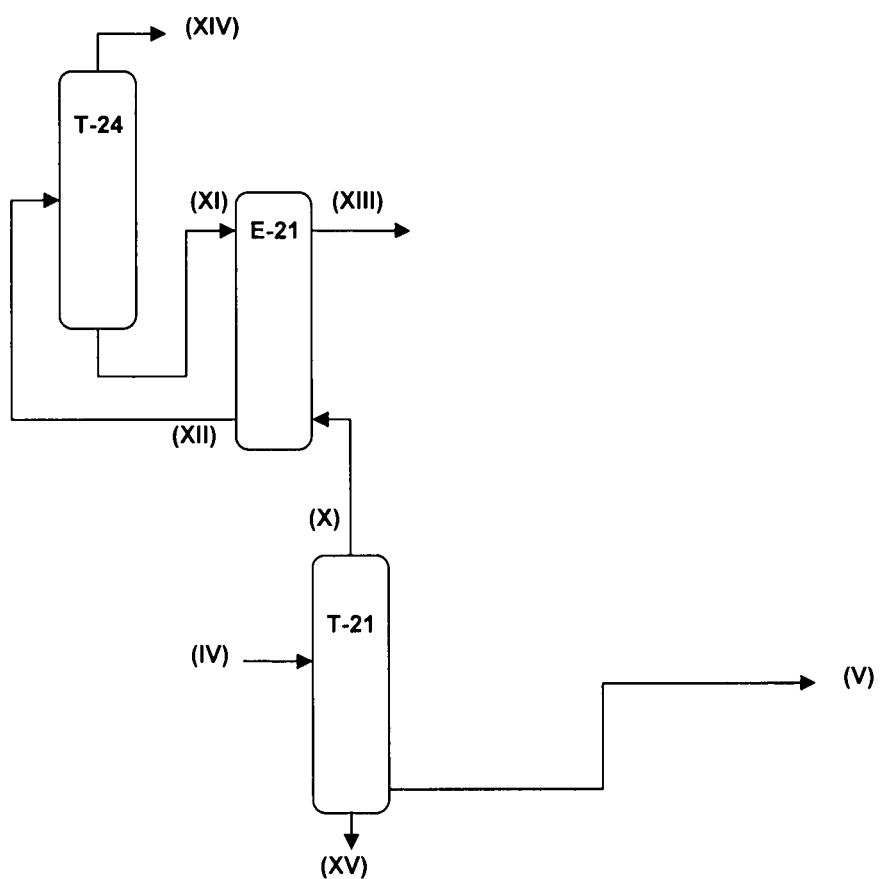

Figure 4: Isolation of MTBE, preferred embodiment [b2]
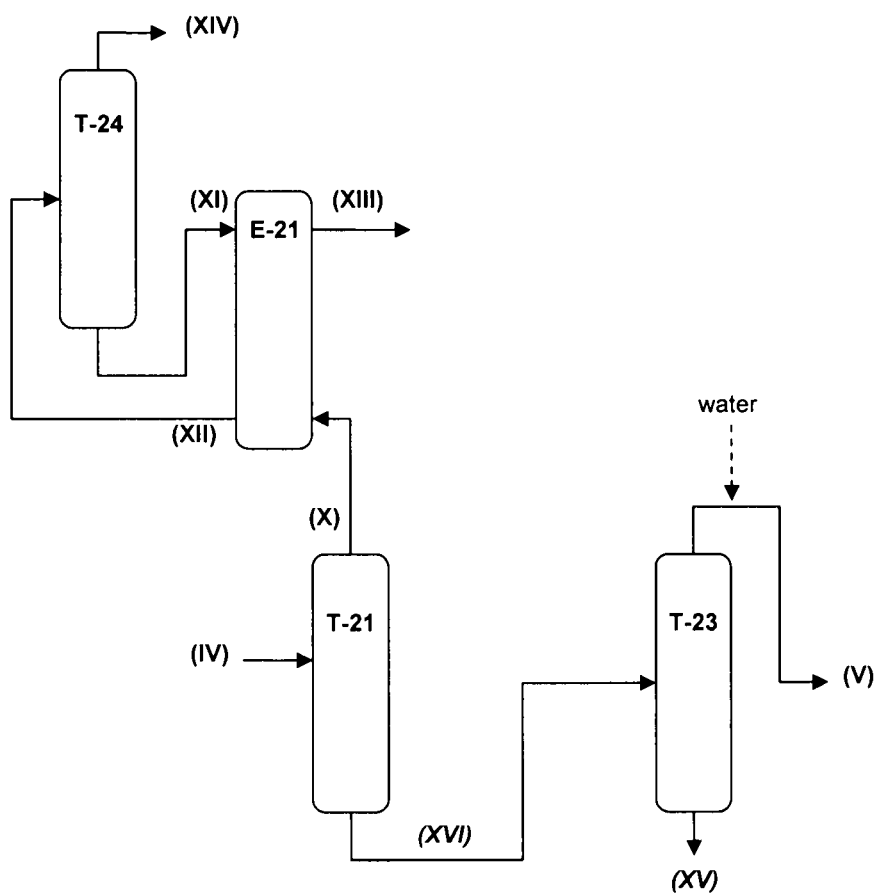

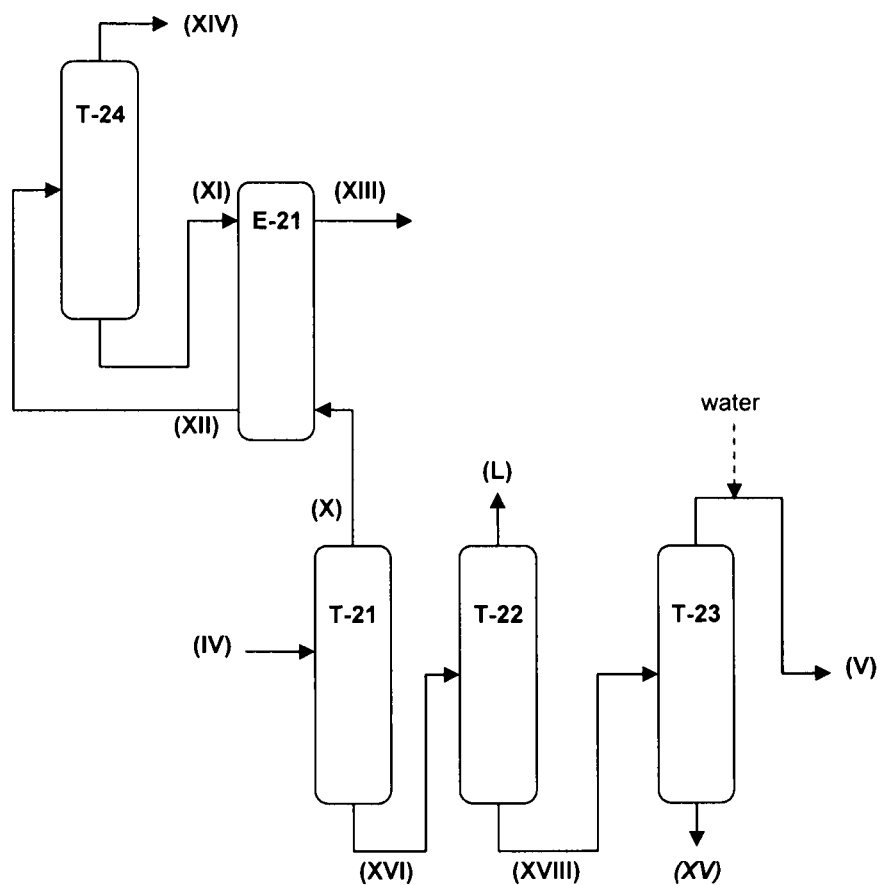
Figure 5: Isolation of MTBE, preferred embodiment [b3]

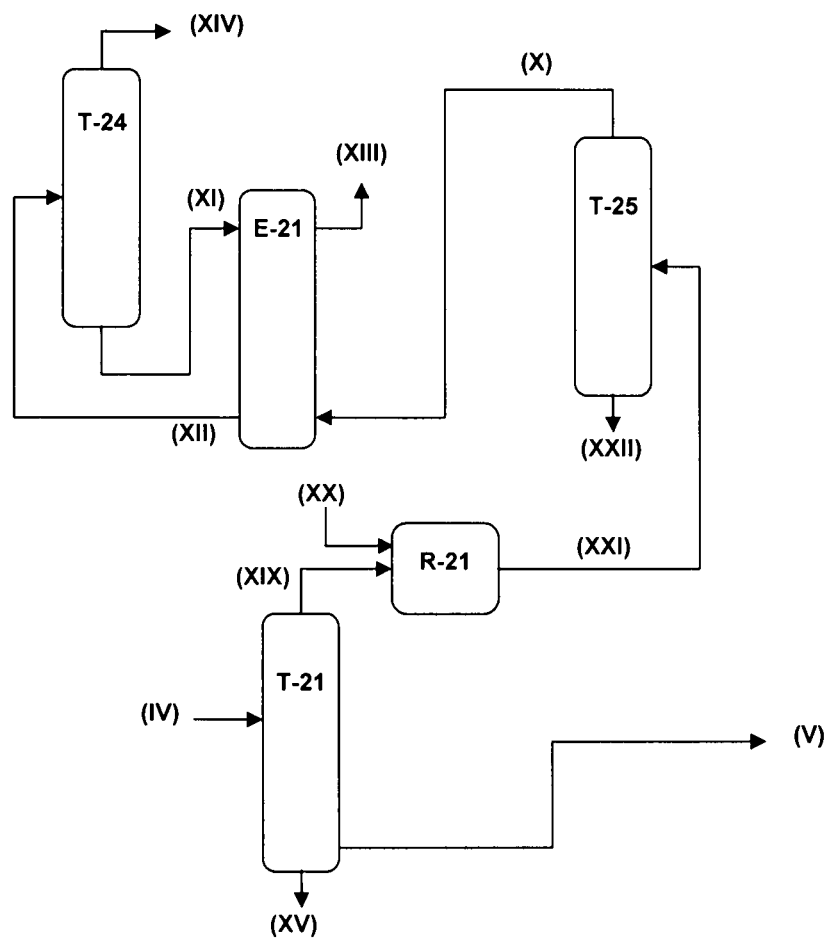
Figure 6: Isolation of MTBE, preferred embodiment [b4]

Figure 7: Isolation of MTBE, preferred embodiment [b5]
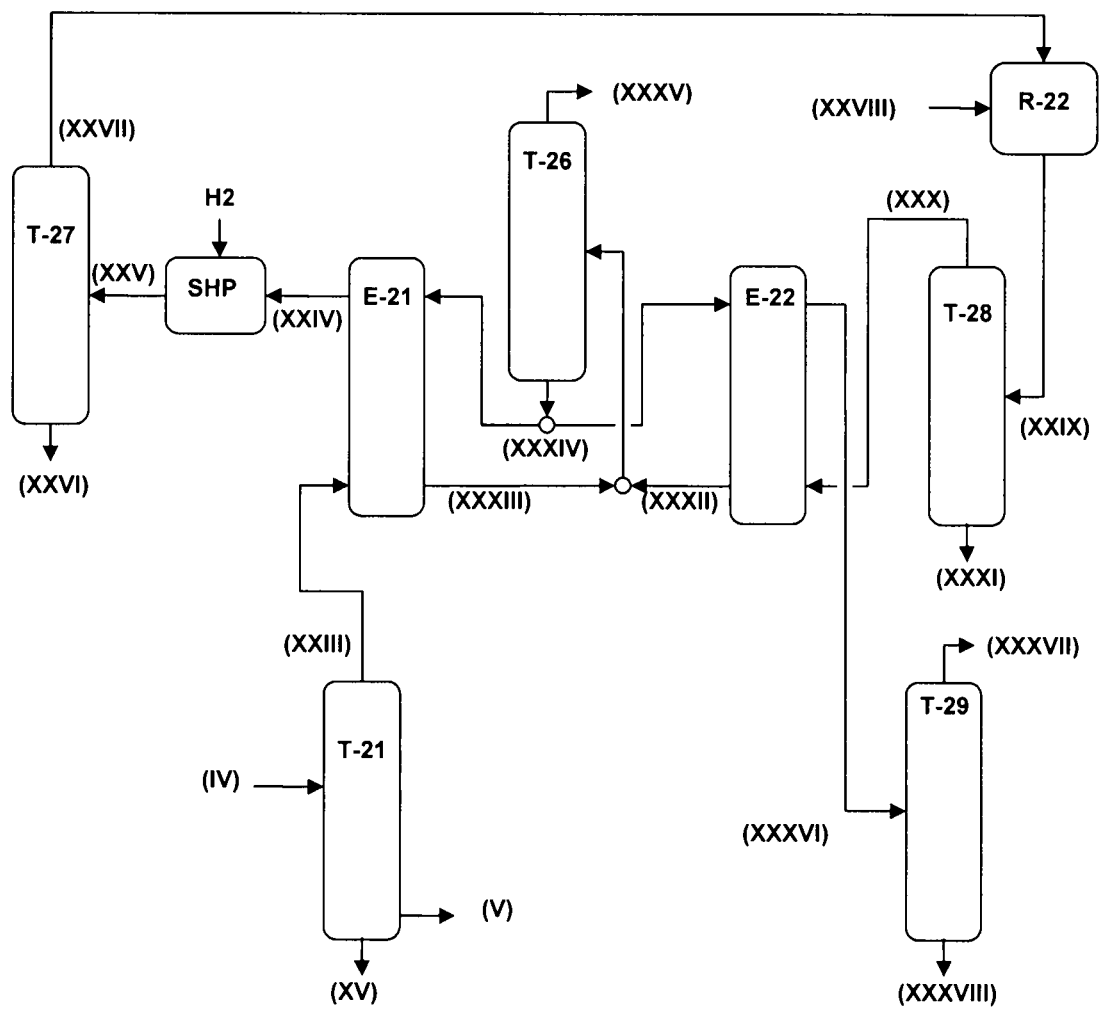

Figure 8: Isolation of isobutene, preferred embodiment [d1]
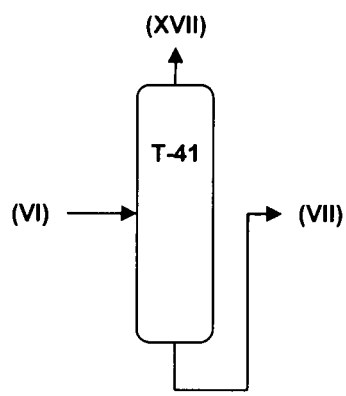
Figure 9: Isolation of isobutene, preferred embodiment [d2]
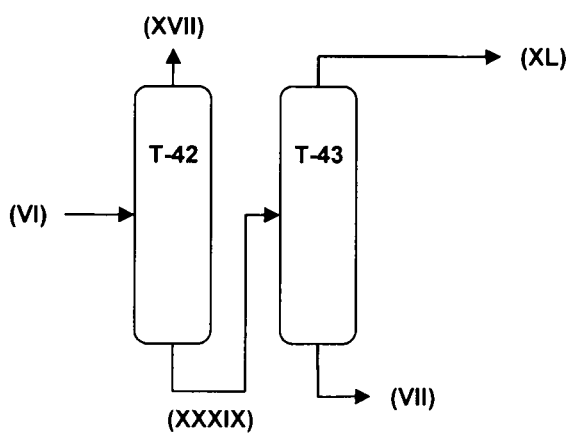

Figure 10: Removal of water, preferred embodiment [e1]
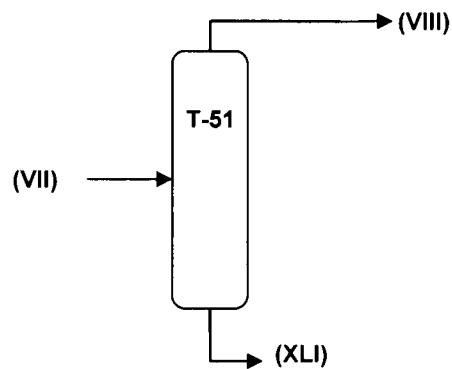
Figure 11: Removal of water, preferred embodiment [e2]
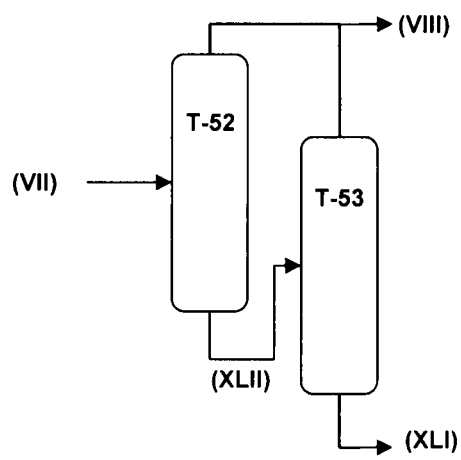

Figure 12: Purification of isobutene
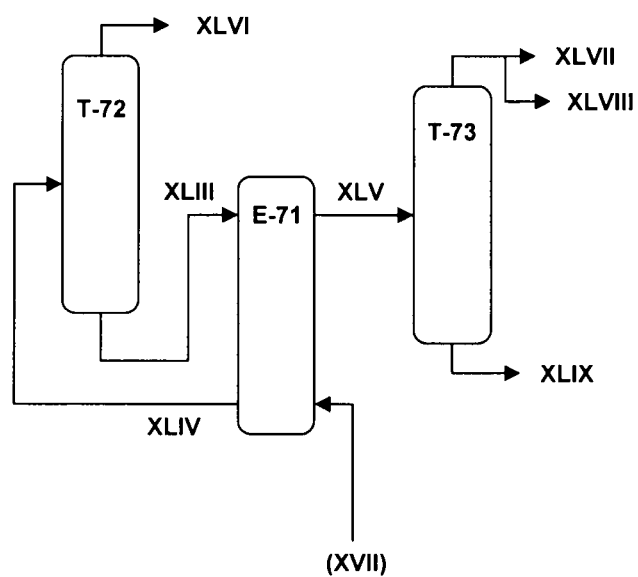

PREPARATION OF ISOBUTENE BY DISSOCIATION OF MTBE

The present invention relates to a process for preparing isobutene by dissociation of MTBE.

Isobutene is a starting material for the production of many products, e.g. for the production of butyl rubber, polyisobutylene, isobutene oligomers and t-butylaromatics. In addition, isobutene can be used as precursor for the preparation of methacrylic acid and esters thereof.

In industrial streams, for example, in the C4 fraction from petroleum crackers, isobutene is frequently present together with saturated and unsaturated $C_4$-hydrocarbons. Isobutene cannot be separated off economically from these mixtures by distillation because of the low boiling point difference or the very low separation factor between isobutene and 1-butene. Isobutene is therefore usually isolated from industrial hydrocarbon mixtures by converting isobutene into a derivative which can easily be separated from the remaining hydrocarbon mixture and re-dissociating the isolated derivative into isobutene and derivatizing agent.

Isobutene is therefore normally separated from $C_4$ fractions from steam crackers as follows: after removal of the major part of the multiply unsaturated hydrocarbons, mainly butadiene, by extraction/extractive distillation or selective hydrogenation to linear butenes, the remaining mixture (raffinate I or hydrogenated cracking $C_4$) is reacted with alcohol or water.

tert-Butanol (TBA) is formed in the reaction of isobutene with water, and an alkyl tert-butyl ether is formed when an alcohol is used, with the alkyl group being determined by the alcohol used. When methanol is used, methyl tert-butyl ether (MTBE) is formed; when ethanol is used, ethyl tert-butyl ether (ETBE) is formed. Both components are primarily used as component for increasing the octane number of spark-ignition fuels. The reaction of isobutene with ethanol to form ETBE has only become industrially relevant in the last decade since legislation prescribes a proportion of renewable raw material in the fuel and bioethanol is available in sufficient quantities. Etherification with C3- or C4-alcohols has likewise been described in the context of processes for preparing isobutene (U.S. Pat. No. 4,287,379; U.S. Pat. No. 4,320,232).

After they have been separated off, both the ethers and TBA can be dissociated into isobutene in a reversal of their formation.

The great advantage of the reaction with alcohols is that a very high conversion of the isobutene can be achieved. This is necessary, in particular, when 1-butene in polymer grade purity is to be isolated from the remaining C4-hydrocarbons, industrially often referred to as raffinate II (Revue De Institut Francais du Petrole, Vol. 46, No. 3, May-June 1991, pages 361-387). The conversion of typically >99.5% necessary here can be achieved in the reaction with methanol in one-stage or multistage reactions (Catalysis Today, 1997, Vol. 34, pages 447-455). In addition, methanol has the advantage that no olefin can be formed from it by elimination of water.

Processes for preparing MTBE have been developed to an increasing extent since the 1970s since MTBE has been used on a large scale as fuel additive for increasing the octane number. A critical step in the development in the following decades was the use of reactive distillation processes. This technique has been used industrially since the 1990s. Despite the very high conversion of isobutene, this technique made it possible to reduce the specific energy consumption. Since then, the MTBE synthesis has evolved to be one of the standard uses for reactive distillation processes (e.g. EP 1 199 296).

Processes for the re-dissociation of the ethers have likewise been known for a long time (DE 1 216 865). However, the dissociation of MTBE has been used on an industrial scale only since the 1980s and, particularly in comparison to the synthesis, only to a limited extent.

The dissociation of MTBE can be carried out in the liquid phase or the gas phase. Typical secondary reactions are the formation of water and dimethyl ether (DME) from methanol and the formation of dimers and oligomers of isobutene (mainly C8-, C12-hydrocarbons).

The C4-hydrocarbons used for the MTBE synthesis are generally saturated with water (about 200-400 ppm of water). In addition, water can get into the synthesis via the alcohol used. The methanol fractions separated off in the MTBE dissociation, in particular, often still contain water from the DME formation in the dissociation.

In the MTBE synthesis, water is converted at least partly into TBA. The TBA formed can be separated off in the purification of the product mixture from the synthesis before dissociation. As a result, this proportion of the isobutene present in the raw material is lost to the preparation of isobutene. The aim of the process of the invention was therefore to utilize at least part of the TBA formed in the synthesis for the preparation of isobutene. It is also known that the introduction of water into the ether synthesis over acidic ion exchangers leads to a significant reduction in the reaction rate (Ind. Eng. Chem. Res 1993, 32, 564-569). However, a sufficient reaction rate in the MTBE synthesis is particularly necessary when the conversion in the ether synthesis has to be high enough to reliably supply a downstream 1-butene production process.

The problem that coupling of an MTBE synthesis with a dissociation from which the alcohol formed is recirculated to the synthesis can lead to accumulation of components in the circuit is known. Although this coupling of synthesis and dissociation is the subject matter of various patents, very little information is given on the removal of these components, in particular not in the case of TBA.

In Hydrocarbon Processing, August 1981, pages 101-106, the authors indicate that recirculation of the methanol from the dissociation to the synthesis is possible as long as a residual amount of at least 30% of MTBE is not utilized in the dissociation in order to discharge secondary components. If the entire amount of MTBE is to be dissociated, an additional "recycle purification unit" becomes necessary. It is not specified which components are discharged and in what way.

U.S. Pat. No. 4,570,026 likewise describes a process with coupled MTBE synthesis and dissociation. Residual amounts of MTBE and oligomers are still present in the recirculated methanol. The oligomers are discharged via an MTBE stream from the synthesis which is not fed to the dissociation.

U.S. Pat. No. 5,567,860 describes the separation of secondary ethers from the dissociation products, with the purified recycle stream obtained being recirculated directly to the dissociation.

The patent EP 0 869 107 discloses a process for preparing 1-butene, isobutene and MTBE. The isobutene is separated off from a mixture of hydrocarbons containing 1-butene and isobutene by formation of MTBE and distillation and a subsequent catalytic dissociation. The products of the dissociation are separated into an isobutene-rich fraction and a fraction containing the major part of the methanol formed, possibly undecomposed ethers and possibly heavy compounds. This fraction is, if appropriate, partly recirculated to the synthesis. In specific embodiments, part of the MTBE is utilized as motor fuel fraction. In the purification of the products from the dissociation reaction as described in the example, water is separated off with the isobutene formed, which still contains proportions of methanol. The major part of the methanol, which may be recirculated to the synthesis, still contains proportions of unreacted MTBE and dimers of isobutene. A further purification of the stream is not described.

Some processes add steam in the dissociation of the ether. Thus, DE 1 934 422 describes a process for separating tertiary monoolefins from hydrocarbon mixtures. Downstream of the reactor, the product mixture is separated in a decanter into an aqueous phase and an organic phase. Residual amounts of alcohol present are separated off by distillation from the aqueous phase and recirculated to the synthesis. The water is reused in the dissociation. In the process variant without addition of steam in the dissociation, a fraction comprising unreacted ethers, alcohol and generally traces of water is recirculated.

The synthesis and dissociation of MTBE are also subject matter of the publication in Catalysis Today, 1997, Vol. 34, pages 447-455. According to this, in particular, an excessive increase in the concentration of 2-methoxybutane (methyl sec-butyl ether, MSBE) in the methanol circuit should be avoided. In addition, there is information on the formation of TBA in the MTBE synthesis and on the re-dissociation of TBA under the conditions of the MTBE dissociation. No information is given on the recirculation or discharge of TBA or limitation of the water concentration.

It was therefore an object of the invention to develop a process for the synthesis and dissociation of MTBE, which makes the isobutene bound in the MTBE synthesis by formation of TBA available to the dissociation and at the same time limits excessive accumulation of TBA and/or water in the synthesis and dissociation.

This object was achieved by a process for preparing isobutene by dissociation of MTBE, which comprises the following steps:
a) MTBE synthesis; reaction of isobutene-containing hydrocarbon mixtures (II), with methanol (III), present in one or more methanol-containing streams (VIII, IX), over acidic ion exchangers to give a stream (IV), containing MTBE and TBA,
b) Isolation of MTBE; separation of a stream (V), containing MTBE and TBA, from stream (IV) by distillation,
c) MTBE dissociation; dissociation of stream (V) in the gas phase over a heterogeneous catalyst to give a stream (VI) containing at least isobutene, methanol, MTBE and water and possibly TBA,
d) Isolation of isobutene; separation of the stream (VI) by distillation to give a stream (VII), containing in each case more than 50% by mass of the amounts of methanol, TBA and water present in stream (VI) and a stream (XVII) containing isobutene,
e) Removal of water; separation of water from stream (VII) to below 1% by mass by distillation to give a stream (VIII),
f) Recirculation; total or partial recirculation of the methanol-containing stream (VIII) to the MTBE synthesis.

The process of the invention is characterized in that the water content is reduced to below 1% by mass in the fraction (VIII) in process step e).

The advantage of the process of the invention is not only the utilization of the isobutene bound as TBA for the dissociation. Only a relatively small amount of wastewater is obtained as additional stream and this can, for example, be passed to a water treatment plant. On the other hand, if TBA were discharged from the process as a separate stream, this would have to be processed separately. The route of isolation or blending into a residual MTBE stream which is marketed, for example as carburettor fuel, as is often indicated in the literature, is possible to only a limited extent. In Europe, for example, the typical specification for marketable MTBE is an ether content of 98%.

Depending on the catalyst used in the process step of dissociation of the ether, there is a risk that the subsequent workup steps will have an acidic pH. The cause can be, for example, the release of traces of acid by the catalyst or the formation of, for example, formic acid as secondary reaction in the dissociation reaction. This can have the consequence that no inexpensive unalloyed steels can be used in these subsequent process steps, but instead it becomes necessary to use higher priced, high alloy steels in order to avoid corrosion caused by the acidic conditions. To avoid this, an alkali stream can be introduced in process step d) or in process step e) of the process of the invention. A further advantage of the process of the invention is that the alkali can be discharged from the process in a simple way together with the water fraction in the removal of water in process step e). There is therefore no risk of the alkali being recirculated to process step a) and here possibly leading to damage to the catalyst used.

The invention further provides a shell-and-tube apparatus having the following elements:
i) bundle of tubes
ii) tube plate,
iii) deflection plates,
iv) inner shell,
v) pressure-bearing outer shell containing at least one inlet and outlet,
vi) space within the shell containing a fluid which gives off or takes up heat, characterized in that the inner shell is joined without leaving a gap or with a small gap to the deflection plates installed over the length of the bundle of tubes and to the tube plate, with the fluid present in the space within the shell enclosing the inner shell on both sides.

Starting Materials

In the process of the invention, it is possible to use all industrial C4-hydrocarbon mixtures which are usually available. Suitable isobutene-containing C4 streams are, for example, light petroleum spirit fractions from refineries, C4 fractions from crackers (for example, steam crackers, hydrocrackers, catalytic crackers), mixtures from Fischer-Tropsch syntheses, mixtures from the dehydrogenation of butanes, mixtures from skeletal isomerization of linear butenes and mixtures formed by metathesis of olefins. These techniques are described in the technical literature (K. Weissermel, H. J. Arpe, Industrielle Organische Chemie, Wiley-VCH, 5th edition, 1998, pages 23 to 24; 65 to 99; 122 to 124).

It is possible to use, for example C4 fractions from steam crackers which are operated primarily for the production of ethene and propene and in which, for example, refinery gases, naphtha, gas oil, LPG (liquefied petroleum gas) and LNG (liquefied natural gas) are used as raw materials or C4 fractions from catalytic crackers. The C4 fractions obtained as by-product contain, depending on the cracking process, varying amounts of isobutene, 1,3-butadiene, 1-butene, c-2-butene, t-2-butene, n-butane and i-butane.

The isobutene-containing C4-hydrocarbons used in the process of the invention preferably have a 1,3-butadiene content of less than 1% by mass, particularly preferably less than 0.5% by mass. Typical isobutene-containing C4-hydrocarbon mixtures are, for example, hydrogenated CC4 (HCC4) and raffinate I. Hydrogenated CC4 is, for example, obtained by means of known industrial processes by selective hydrogenation of the multiply unsaturated hydrocarbons present in the CC4. For example, mainly 1-butene and 2-butenes are formed from 1,3-butadiene.

Raffinate I is obtained by separating 1,3-butadiene and other multiply unsaturated hydrocarbons from the CC4. This can be effected by known methods, for example by extractive distillation.

Table 1 below indicates typical proportions by mass of the main components of CC4, HCC4 and raffinate I.

TABLE 1

Typical composition of CC4, HCC4 and raffinate I.

| Component | CC4 (S) | HCC4 | Raffinate I |
|---|---|---|---|
| Isobutane | 0.6-6 | 0.6-6 | 1-10 |
| n-Butane | 0.5-8 | 0.5-10 | 0.8-13 |
| 1-Butene | 9-25 | 24-67 | 15-42 |
| Isobutene | 10-35 | 10-35 | 17-58 |
| 2-Butenes | 4-20 | 14-48 | 6-33 |
| 1,3-Butadiene | 25-70 | 0-1 | 0-1 |
| C1-C3-HCs | 0-1 | 0-1 | 0-2 |

Notes:
CC4 (S): typical for a C4 mixture obtained from the cracking C4 from a steam cracker (high severity) without additional moderation of the catalyst.
HCs: hydrocarbons
All figures in % by mass The mixture of C4-hydrocarbons obtained after partial or complete separation of isobutene from raffinate I or HCC4 is generally referred to as raffinate II. The residual isobutene content of raffinate II varies with the method of separating off isobutene and is normally less than 5% by mass. Typical methods of separating off the isobutene are, apart from the ether synthesis (MTBE, ETBE), the synthesis of TBA and the dimerization of isobutene.

Process Step a): MTBE Synthesis

In process step a) of the process, isobutene (I) present in a mixture with other C4-hydrocarbons is introduced as isobutene-containing C4-hydrocarbons (II). In the process of the invention, particular preference is given to using HCC4, raffinate I, mixtures of these or mixtures of these with raffinate II streams as isobutene-containing C4-hydrocarbons (II). The C4-hydrocarbon streams used can contain water up to the saturation point. A water content of 200-400 ppm is typical. In addition, the C4-hydrocarbon streams are preferably washed with water in order to remove polar components, after which the C4 streams are saturated with water before use in process step a). Water present in heterogeneous form is preferably separated off, for example by means of a decanter with or without coalescence-promoting internals, before use in process step a).

In process step a) of the process of the invention, the isobutene (I) present in the isobutene-containing C4-hydrocarbons (II) is reacted with methanol (III) over acidic ion exchangers to give an MTBE- and TBA-containing reaction mixture (IV). In principle, all known methods of synthesizing MTBE can be used for this purpose; for example, the MTBE synthesis can be carried out in a manner analogous to the description in DE 101 02 082.

The MTBE synthesis in process step a) is preferably carried out in at least two, particularly preferably three, fixed-bed reactors. As reactors in which the methanol (III) is reacted with the isobutene (I) to close to the thermodynamic equilibrium, it is possible to use conventional fixed-bed reactors (shell-and-tube reactors, adiabatic fixed-bed reactors, circulation reactors). They can be operated with or without partial recirculation, and if appropriate with cooling of the recycle stream. An MTBE- and TBA-containing reaction mixture (IV) containing, inter alia, unreacted C4-hydrocarbons, 2-methoxybutane, C8-hydrocarbons, DME and residual amounts of methanol as further constituents is taken off from the last of the fixed-bed reactors.

The conversion of the isobutene is if possible carried out to achievement of the thermodynamic equilibrium of MTBE, methanol and isobutene, with an isobutene conversion of preferably greater than 90%, particularly preferably greater than 95%, very particularly preferably greater than 98%, being set or achieved. The reactors are preferably operated at a temperature of from 20 to 110° C., preferably 25 to 70° C. and a pressure of from 0.5 to 5 MPa, preferably from 0.7 to 2 MPa (abs).

Since the thermodynamic equilibrium between methanol/isobutene and ether is predominantly on the side of the ether at low temperature, the first of the reactors is preferably operated at a higher temperature in order to achieve a high reaction rate than the subsequent reactors in which the equilibrium position is exploited. Preference is given to operating the first of the reactors at a temperature of from 35 to 70° C. and operating the subsequent reactors at a temperature of from 25 to 50° C.

The methanol (III) is fed as one or more methanol-containing streams which can additionally contain further components into the reaction in step a). For example, the following methanol-containing streams can be utilized: fresh methanol, i.e. methanol which has not been recovered in the process of the invention (to compensate for methanol losses due to discharge of MTBE or formation of DME), the methanol-containing fraction (VIII) and streams obtained in the fractionation of water and methanol from extractions. Methanol (III) is, for the purposes of the present invention, the sum of the pure methanol present in these streams.

Further components which can be present in these streams are, for example, MTBE, TBA, water, C8-hydrocarbons and isoprene.

It is naturally possible to feed the streams in separately at various places in the process. However, they are preferably mixed and utilized as a joint stream.

The molar ratio of methanol (III) to isobutene in the feed to the first reactor or process step a) is preferably in the range from 10:1 to 1:1, particularly preferably from 5:1 to 1.1:1 and very particularly preferably in the range from 1.8:1 to 1.2:1.

Catalysts used in the MTBE synthesis are solid acidic ion-exchange resins having sulphonic acid groups. Suitable ion-exchange resins are, for example, those produced by sulphonation of phenol-aldehyde condensates or of cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, cooligomers formed by reaction of styrene with divinylbenzene are used as precursors for the production of ion-exchange resins having sulphonic acid groups. The resins can be prepared in gel, macroporous or sponge form. The properties of these resins, in particular specific surface-area, porosity, stability, swelling or shrinkage and exchange capacity can be varied via the production process.

The pore volume of the ion-exchange resins used as catalysts is preferably from 0.3 to 0.9 ml/g, in particular from 0.5 to 0.9 ml/g. The particle size of the resins is preferably from 0.3 mm to 1.5 mm, in particular from 0.5 mm to 1.0 mm. The particle size distribution can be made narrower or broader. Thus, for example, ion-exchange resins having a very uniform particle size (monodisperse resins) can be used. The capacity of the ion exchanger is, based on the form as supplied, preferably from 0.7 to 2.0 eq/l, in particular from 1.1 to 2.0 eq/l, or preferably from 0.5 to 5.5 mol/kg, in particular from 0.8 to 5.5 mol/kg. The capacities in mol/kg are in each case based on the ion-exchange resin dried to constant weight in a stream of hot nitrogen at, for example, 105° C.

In the process of the invention, the ion-exchange resins can be used in their H form. Strongly acidic resins of the styrene-divinylbenzene type, which are preferably used, are sold, inter alia, under the following trade names: Amberlyst® 15, Amberlyst® 35 (each Rohm & Haas) or Lewatit® K2621 (Lanxess).

Process Step b): Isolation of MTBE

The separation of the MTBE- and TBA-containing fraction (V) from the reaction mixture (IV) by distillation can in the simplest case be carried out in a single column. Here, the fraction (V) is obtained as bottom product. The distillate consists mainly of unreacted C4-hydrocarbons, which owing to azeotrope formation with methanol also contain methanol, and DME. The bottom product contains not only TBA and MTBE but also 2-methoxybutane and C8-hydrocarbons. Depending on the methanol (III)/isobutene (I) ratio selected and the conversion achieved, methanol can also be present.

The distillation column preferably has from 15 to 55 theoretical plates, more preferably from 20 to 40 and particularly preferably from 25 to 35. The feed to the column is preferably introduced between plate 10 and plate 30 (from the top), more preferably between plates 15 and 25. The column is preferably operated at a pressure of from 0.3 to 2.5 MPa(abs), more preferably from 0.5 to 1.0 MPa(abs). The reflux ratio is, depending on the number of theoretical plates realized, the composition of the reactor output and the required purities of distillate and bottom product, preferably less than 5, more preferably less than 2. The reflux ratio is defined as the ratio of the runback stream into the column to the distillate stream discharged.

In a preferred embodiment AFF1, the MTBE- and TBA-containing fraction (V) is taken off as a side offtake stream from the column. A fraction in which C8-hydrocarbons are concentrated and are thus discharged from the process is obtained as bottom product. The removal of C8- and, if appropriate C8+-hydrocarbons has the advantage that none or very little of this gets into the dissociation reactor. The catalyst in the MTBE-dissociation is thus protected against fouling by high boilers, as a result of which the risk of a reduction in activity and a shortening of the operating life of the catalyst is reduced.

A distillation column in which the MTBE- and TBA-containing fraction (V) is taken off as side offtake stream, preferably has from 20 to 65 theoretical plates, more preferably from 25 to 55 and particularly preferably from 30 to 45. The feed to the column is preferably introduced between plate 10 and plate 30 (from above), more preferably between plates 15 and 25. The side stream is preferably taken off below the point at which the feed is introduced, more preferably from 5 to 25 plates below, particularly preferably from 10 to 20 plates below, the point at which the feed is introduced, and preferably from 5 to 20 plates above the bottom offtake, preferably from 10 to 15 plates above the bottom offtake. The column is preferably operated at a pressure of from 0.3 to 2.5 MPa(abs), more preferably from 0.5 to 1.0 MPa(abs). The reflux ratio is, depending on the number of theoretical plates realized, the composition of the reactor output and the required purities of distillate and bottom product, preferably less than 5, more preferably less than 2.

In a further preferred embodiment AFF2 of process step b), the column is configured as a reactive distillation. This has the advantage that additional isobutene which has not reacted in process step a) is converted into MTBE.

The reactive distillation column is operated in a pressure range from 0.3 to 2.5 MPa(abs), preferably from 0.5 to 1.0 MPa(abs) and at a temperature in the reaction zone of from 50 to 90° C., preferably from 55 to 70° C. at a reflux ratio in the range from 0.5 to 1.5, preferably from 0.7 to 0.9.

The reactive distillation column preferably has a region of a purely distillative separation above the catalyst packing. The zone above the catalyst packing preferably has from 5 to 25 theoretical plates, in particular from 10 to 15 theoretical plates. The separation zone below the catalyst comprises from 10 to 40, in particular from 20 to 30, theoretical plates.

The feed to the reactive distillation column can be introduced above or below, preferably below, the catalyst zone. The feed to the reactive distillation column is preferably introduced below the reactive packing, preferably from 3 to 13 theoretical plates below, particularly preferably 4 to 10 theoretical plates below, the reactive packing.

The catalyst zone can be estimated to have a distillative action of from 1 to 5 theoretical plates per meter of packing height. The height of the catalyst zone/reactive zone can be determined as a function of the desired isobutene conversion by means of simple preliminary experiments. The amount of catalyst is preferably selected so that an isobutene conversion of from 75 to 99%, preferably from 85 to 98% and particularly preferably from 95 to 97%, based on the isobutene content in the feed to the reactive distillation is achieved.

As in process step a), an acidic ion-exchange resin is used as catalyst. In the reactive distillation column, the catalyst can either be integrated into the packing, for example, KataMax® (as described in EP 0 428 265), KataPak® (as described in EP 0 396 650 or DE 298 07 007.3 U1), or polymerized on to shaped bodies (as described in U.S. Pat. No. 5,244,929).

The hydraulic loading in the catalytic packing of the column is preferably from 10% to 110%, more preferably from 20% to 70%, of its flooding point loading. For the purposes of the present invention, the hydraulic loading of a distillation column is the uniform hydrodynamic loading of the column cross section by the ascending vapour stream and the descending liquid stream. The upper loading limit characterizes the maximum loading by vapour and runback liquid above which the separation performance decreases as a result of entrainment or banking-up of the runback liquid by the ascending vapour stream. The lower loading limit characterizes the minimum loading below which the separation performance decreases or breaks down as a result of irregular flow or empty running of the column, e.g. the trays. (Vauck/Müller, "Grundoperationen chemischer Verfahrenstechnik", p. 626, VEB Deutscher Verlag für Grundstoffundustrie).

At the flooding point, the shear stresses imparted by the gas to the liquid become so great that all of the liquid is entrained in the form of droplets in the gas or that phase inversion occurs in the column (J. Mackowiak, "Fluiddynamik von Kolonnen mit modernen Füllkörpern and Packungen für Gas/Flussigkeitssysteme", Otto Salle Verlag 1991).

The reactive distillation technique for further isobutene conversion enables, in particular residual isobutene concentrations of less than 1000 ppm by mass (wppm), preferably 800 wppm and particularly preferred less than 500 wppm, based on the C4 mixture in the distillate, to be obtained.

More methanol than is consumed for complete reaction of the isobutene still present can be present in the feed to the column. However, the methanol excess should be limited in such a way that, firstly, a sufficient amount of methanol for formation of the azeotrope of methanol and C4-hydrocarbons is present and secondly, not so much that an excessive amount of methanol gets into the bottom product, so that an MTBE having a methanol content of preferably less than 10 000 wppm, particularly preferably less than 5000 wppm, is obtained.

Additional methanol can optionally be fed into the reactive distillation column. This can be introduced together with the feed stream from process step a) or else at a different point or a plurality of points on the reactive distillation column, e.g. at the top of the column and/or on, between and/or under the catalyst bed.

The methanol-containing C4-hydrocarbons separated off as distillate can be processed further in various work-up variants.

In a preferred work-up variant, the methanol is separated off from the methanol-containing C4-hydrocarbons obtained as distillate. The separation of the methanol from the overhead product can, in particular, be carried out by extraction with water or an aqueous solution as washing medium. Preference is given to using an aqueous solution having a pH of greater than or equal to 8, preferably from 8 to 12. The pH can be set, for example, by addition of the sodium hydroxide and/or sulphuric acid. This extraction can be carried out according to the known standard methods of industry, for example in an extraction column or in a cascade of mixers and settlers. The methanol is preferably separated off by means of water or an aqueous solution as washing medium in an extraction column. The residual alcohol content is preferably reduced to below 0.2% by mass, particularly preferably to below 500 wppm, very particularly preferably to below 50 wppm. The extraction column preferably has from 2 to 25, particularly preferably from 5 to 15, theoretical plates and is preferably operated at temperatures of from 10 to 90° C. and pressures of at least 0.1 MPa above the vapour pressure of the C4-hydrocarbons. The mass ratio of washing medium to overhead product fed in (industrial mixture IV plus methanol) is preferably from 1:5 to 1:40.

The alcohol-laden washing water from the extraction is preferably worked up in a separate unit and the water is at least partly recirculated to the extraction. The work-up can be carried out, for example, by means of a distillation in which a virtually alcohol-free water fraction is obtained at the bottom and methanol is obtained as overhead product. The methanol can be returned to step a) of the process of the invention.

The methanol-free C4-hydrocarbons obtained from the extraction can be worked up by known methods to give high-purity 1-butene. For this purpose, for example, traces of multiply unsaturated hydrocarbons are firstly hydrogenated in a selective hydrogenation (e.g. DE 31 43 647) and firstly n-butane and 2-butenes, then isobutane and further low boilers are subsequently separated from the 1-butene by double fractionation. The 2-butenes separated off in the first fractionation and the n-butane can, for example, be processed further in an oligomerization to give C8-olefins (e.g. OCTOL process, see Hydrocarbon Process, Int. Ed. (1986) 65, p. 31-33) or in a hydroformylation to give valeraldehyde.

In a second preferred work-up variant for the C4-hydrocarbons which have been separated off, these are firstly fed to a further reaction stage in order to reduce the isobutene content further. This reaction is preferably carried out in one or two adiabatic fixed-bed reactors, using the same catalysts as in process step a). The temperatures at which the reaction is carried out are preferably from 20 to 60° C., more preferably 30-50° C., and the pressure is preferably from 0.5 to 5 MPa, more preferably from 0.7 to 2 MPa. Preference is given to feeding additional methanol into the reaction stage, so that the methanol content at the outlet of the reactors is preferably 1-10% by mass.

The output from the reaction stage is separated in a distillation column to give methanol-containing C4-hydrocarbons as distillate. This distillation, too, can be carried out as a reactive distillation. The C4-hydrocarbons can be processed further by extraction, selective hydrogenation and distillation in a manner analogous to the first work-up variant. The bottom product obtained is an MTBE stream which normally still contains methanol. It can be utilized separately or can be recirculated in its entirety or partly to process step a).

In the work-up according to this second work-up variant, the separation of the reaction mixture (IV) by distillation can be carried out with a lower outlay so that proportions of MTBE still remain in the distillate stream. The energy input required can be reduced in this way.

In a further preferred embodiment, AFF3 of process step b), the MTBE bottom product from the first column for separation of the reaction mixture (IV) is purified further in a second column. In this column, high boilers, especially C8-hydrocarbons, are removed as bottom product. A further task of this column can be to separate off part or all of the 2-methoxybutane since 2-methoxybutane can be dissociated into linear butenes and methanol in the reactor. Linear butenes may, if their concentration becomes too high, put the isobutene specification at risk.

The column is operated at a pressure which allows the major part of the TBA present in the feed to get into the distillate (formation of a pressure azeotrope). The column pressure is therefore preferably in the range from 0.3 to 2.0 $MPa_{(abs)}$ regardless of whether only DIB or additionally 2-methoxybutane is to be separated off. When the dissociation of the MTBE- and TBA-containing fraction (V) obtained at the top of the column is carried out in the gas phase at elevated pressure in the dissociation reactor, it can be advantageous to carry out the distillation at a higher pressure, in which case the overhead condenser is preferably operated as a partial condenser and the overhead product (V) is taken off in vapour form. The overhead product which has been taken off in vapour form can then be fed either directly or after further preheating to the reactor. The pressure difference between distillation and reactor is preferably at least 0.05 $MPa_{(abs)}$. If the reaction pressure in the dissociation reactor is, for example, 0.7 $MPa_{(abs)}$, the distillation pressure should preferably be at least 0.75 $MPa_{(abs)}$. At operating pressures of greater than 0.95 $MPa_{(abs)}$, (low pressure) steam can be generated by means of the heat of condensation and can be used to heat the other columns of the process. Depending on the operating pressure selected, steam or heat transfer oil can be used for heating the column.

When, in particular, only C8-hydrocarbons are to be separated off in the column, it can be advantageous for the column to have from 15 to 60 theoretical plates, preferably from 20 to 55 theoretical plates and more preferably from 30 to 45 theoretical plates. The reflux ratio, which for the purposes of the present invention is defined as the mass flow of runback divided by the mass flow of distillate, is preferably set to a value of from 0.5 to 7, preferably from 1 to 4, depending on the number of theoretical plates realized, the composition of the MTBE used and the required purity.

If DIB and in addition 2-methoxybutane are to be separated off in the column, the distillation column used preferably has from 50 to 140 theoretical plates, more preferably from 60 to 120 and very particularly preferably from 80 to 110. The reflux ratio is, depending on the number of theoretical plates realized, the composition of the MTBE used and the required purity, preferably from 1 to 20, more preferably from 3 to 10.

Even if 2-methoxybutane is not necessarily to be separated off, the design of the column with a higher number of theoretical plates does not have to be a disadvantage since part of the higher capital costs for the larger column can be compensated for by an energy saving (reduction in the reflux ratio). At the same time, a higher operational flexibility is achieved as a result.

The bottom product from the column contains the high boilers diisobutene and 2-methoxybutane and also MTBE. If, primarily diisobutene is to be separated off in the column, the MTBE content of the bottom product can be reduced to values below 25% by mass. If 2-methoxybutane is to be additionally separated off, a higher MTBE content of from 60 to 85% by mass is advantageously permitted in the bottom product because of the small boiling point difference between 2-methoxybutane and MTBE, in order to reduce the outlay for the separation.

In both cases, this mixture can be utilized thermally, be employed as starting material for a synthesis gas plant or be used either directly or after hydrogenation as fuel component.

In a further preferred embodiment AFF4 of process step b), a further distillation column for separating off by-products is installed between the two columns of AFF3. In this further column, intermediate-boiling components are separated off in their entirety or partly as distillate at the top. For the purposes of the present invention, intermediate-boiling components are components having a boiling point between that of the C4-hydrocarbons and MTBE or the MTBE/methanol azeotrope. Examples are dimethoxymethane and C5-hydrocarbons such as n-pentane, isopentane, neopentane, 1-pentene, 2-pentene, 3-methyl-1-butene and isoprene. Any residual C4-hydrocarbons still present are separated off together with the intermediate-boiling components. The proportion of intermediate-boiling components in the feed to the column is generally not high and is preferably below 2%, more preferably below 0.5%.

The alternative to the removal of the intermediate-boiling components would be removal together with the generally much larger amount of C4-hydrocarbons via the distillate of the first column. However, they could be separated off from the latter by distillation only as bottom product. Since the entire C4-hydrocarbons would have to be distilled off overhead for this purpose, this option would be energetically less favourable.

The distillation column for separating off the intermediate-boiling components preferably has from 30 to 75 theoretical plates, more preferably from 40 to 65 theoretical plates and particularly preferably from 40 to 55 theoretical plates. The column is preferably operated, depending on the number of theoretical plates realized, the composition of the MTBE used and the required purity in respect of intermediate-boiler components, at a reflux ratio in the range from 150 to 350, in particular from 200 to 300. The column is preferably operated at an operating pressure of from 0.2 to 0.6 $MPa_{(abs)}$, more preferably from 0.3 to 0.4 $MPa_{(abs)}$. The column can be heated using, for example, steam. Condensation can, depending on the operating pressure selected, be effected against cooling brine, cooling water or air. The overhead vapours from the column can be condensed completely or only partially, so that the overhead product can be taken off in either liquid or vapour form. The overhead product can, for example, be utilized thermally or be employed as starting material for a synthesis gas plant.

The MTBE- and TBA-containing fraction (V) separated off in process step b) preferably has an MTBE content of greater than 95% by mass, particularly preferably greater than 98% by mass. The proportion of TBA is preferably from 0.05 to 5% by mass, more preferably from 0.2 to 2.0% by mass, very particularly preferably from 0.2 to 1.0% by mass. Methanol can be present in addition to MTBE and TBA, preferably in an amount of from 0 to 5% by mass, more preferably from 0.1 to 1% by mass.

Concentration and occurrence of further components are greatly dependent on the raw materials used in process step a) and the process conditions in steps a) and b). The 2-methoxybutane content is preferably from 0 to 1.0% by mass, more preferably from 0.05 to 0.5% by mass, particularly preferably from 0.08 to 0.3% by mass. The content of C8-hydrocarbons is preferably from 0 to 1% by mass, more preferably from 0 to 0.1% by mass, particularly preferably from 0 to 0.01% by mass.

Typical other components present are 3-methoxy-1-butene, 1-methoxy-2-butene, dimethoxymethane and C5-hydrocarbons.

Process Step c): MTBE Dissociation

In step c) of the process of the invention, all or part of the MTBE- and TBA-containing fraction (V) is fed to a dissociation reaction where it is dissociated into dissociation products (VI) containing at least isobutene, methanol, MTBE and water and possibly TBA in the gas phase over a heterogeneous catalyst. It is possible here to use all solid catalysts which bring about the dissociation of MTBE into isobutene and methanol in the temperature range from 120 to 400° C., in particular the range from 180 to 350° C.

The process of the invention is preferably carried out so that a very large part of the MTBE produced in step a) is fed to step c). It is therefore particularly suitable for the production of pure isobutene from isobutene-containing C4-hydrocarbons when a high proportion of the isobutene present in the C4-hydrocarbons is to be obtained as pure isobutene. As an alternative, proportions of the MTBE-rich streams occurring in the process can be used in another way, for example, for use as fuel additive. However, particular preference is given to feeding at least 80% by mass, very particularly preferably at least 90% by mass, of the MTBE present in the reaction mixture (IV) to step c) via the fraction (V).

The catalysts used in the process of the invention can be, for example, metal oxides, mixed metal oxides, in particular those containing silicon oxide and/or aluminium oxide, acids on metal oxide supports or metal salts or mixtures thereof.

In the process of the invention, preference is given to using catalysts which formally consist of magnesium oxide, aluminium oxide, and silicon oxide for the dissociation of MTBE into isobutene and methanol in the gas phase. Such catalysts are described, for example, in U.S. Pat. No. 5,171,920 in Example 4 or in EP 0 589 557.

Particular preference is given to using catalysts which formally comprise magnesium oxide, aluminium oxide and silicon dioxide and have a proportion of magnesium oxide of from 0.5 to 20% by mass, preferably from 5 to 15% by mass and more preferably from 10 to 15% by mass, a proportion of aluminium oxide of from 4 to 30% by mass, preferably from 10 to 20% by mass and a proportion of silicon dioxide of from 60 to 95% by mass, preferably from 70 to 90% by mass. It can be advantageous for the catalyst to comprise an alkali metal oxide in addition to the magnesium oxide. This alkali metal oxide can be selected, for example, from among $Na_2O$ and $K_2O$. The catalyst preferably comprises $Na_2O$ as alkali metal oxide. The preferred catalyst preferably has a BET surface area (determined volumetrically by means of nitrogen in accordance with DIN ISO 9277) of from 200 to 450 $m^2/g$, more preferably from 200 to 350 $m^2/g$. If the catalyst according to the invention is applied as active composition to a support, only the active composition has a BET surface area in the stated range. The material composed of catalyst and support can, on the other hand, have a significantly different BET surface area, in particular a lower BET surface area, depending on the nature of the support.

The pore volume of the catalyst is preferably from 0.5 to 1.3 ml/g, more preferably from 0.65 to 1.1 ml/g.

The average pore diameter (preferably determined by a method based on DIN 66133) of the catalyst is preferably from 5 to 20 nm, more preferably from 8 to 15 nm. Particular preference is given to at least 50%, preferably over 70%, of the total pore volume (sum of the pore volume of pores having a pore diameter greater than or equal to 3.5 nm determined by mercury porosimetry in accordance with DIN 66133) of the catalyst being made up by pores having a diameter of from 3.5 to 50 nm (mesopores).

In the process of the invention, preference is given to using catalysts which have an average particle size (determined by sieve analysis) of from 10 μm to 10 mm, more preferably from 0.5 mm to 10 mm, particularly preferably an average particle size of from 1 to 5 mm. Preference is given to using solid catalysts which have an average particle size $d_{50}$, of from 2 to 4 mm, in particular from 3 to 4 mm.

In the process of the invention, the catalyst can be used as shaped bodies. The shaped bodies can have any shape. The catalyst is preferably used as shaped bodies in the form of spheres, extrudates or pellets. The shaped bodies preferably have the abovementioned average particles sizes.

The production and use of such magnesium-aluminosilicate catalysts is described in DE 10 2006 040432.7. This is incorporated by reference.

It can be advantageous in terms of the activity and/or selectivity of some catalysts for proportions of water to be added to the feed to the reactor. Thus, for example, JP 19912201 describes the continuous addition of water to an aluminosilicate doped with alkali metal or alkaline earth metal in order to reduce the formation of secondary components.

In the process of the invention, the addition of water to the feed to the reactor can be effected by, for example, addition of water to the stream (V). This is effected, for example, directly by addition of water or water vapour to the gaseous stream (V), which is fed into the reactor. If the stream (V) is vaporized separately upstream of the reactor, water can be added at this point.

A further possibility is to add the water in process step b) in the isolation of the MTBE- and TBA-containing fraction (V). The water is in this case preferably fed into the feed to the column or into the runback of the column. This is particularly preferably carried out in the column, in which the stream (V) is separated off.

The optional addition of water to moderate the catalyst is carried out in such a way that the proportion of water in stream (V) is preferably from 0 to 5% by mass, particularly preferably from 0.2 to 1.5% by mass.

As added water, preference is given to using fully demineralized or distilled water or water vapour.

The dissociation of the MTBE is carried out in the gas phase in the temperature range from 120 to 400° C., in particular from 180 to 350° C. at pressure of from 0.1 to 2 MPa(abs), in particular at pressures of from 0.3 to 1 MPa (abs), very particularly preferably at pressures of from 0.5 to 0.8 MPa(abs).

The dissociation of MTBE into isobutene and methanol is an endothermic reaction, which means that the reaction mixture is cooled during the reaction. The reactor is preferably operated in such a way that no partial condensation of MTBE and products on the catalyst occurs under the pressure conditions selected. The reactor is particularly preferably carried out so that the minimum temperature in the reactor at any point in the catalyst bed is greater than 150° C., very particularly preferably greater than 200° C. The maximum temperature decrease can be set via numerous parameters, e.g. via the temperature of the heat transfer medium used for heating and by means of the rate at which the heat transfer medium flows through the jacket. The temperature profile in the catalyst bed is preferably monitored by means of a sufficient number of temperature measurements.

During operation, it can be advantageous to increase the inlet temperature and/or operating temperature with increasing deactivation of the catalyst in order to keep the conversion constant.

The conversion of the MTBE in step c) of the process of the invention is in the range from 40% to 98%, preferably from 75% to 97%, particularly preferably from 85% to 95%.

Under the conditions for the dissociation of MTBE, TBA is likewise at least partly dissociated. The conversion is limited by the position of the equilibrium of the reaction at the respective temperature.

The reactor is preferably operated in a single pass at a space velocity (Weight Hourly Space Velocity (WHSV) in kilogram of starting material per kilogram of catalyst per hour) of from 0.1 to 5 h$^{-1}$, in particular from 1 to 3 h$^{-1}$.

As reactors, preference is given to using tube reactors or shell-and-tube reactors, in particular those having internal tube diameters of from 10 to 60 mm.

The tubes are heated via the reactor shell by means of steam, salt melts or heat transfer oils. Particularly when using liquid heating media, the shell side is constructed so that a very homogeneous temperature gradient is present at all tubes. The technical measures necessary for this are known to those skilled in the art and are described in the literature (installation of deflection plates, disc-and-doughnut construction, introduction/discharge of the heat transfer medium at various points on the reactor, etc.). Reaction medium and heat transfer medium are preferably conveyed in cocurrent, particularly preferably from the top downward, through the tractor tubes or the reactor shell. A preferred embodiment is described, for example, in DE 10 2006 040433.5.

In conventional shell-and-tube apparatuses, deflector plates are used on the shell side in order to deflect the flow of the heat transfer fluid which actually runs parallel to the tubes into a transverse direction. This improves heat transfer and, in addition, significantly increases the flow path length. However, manufacturing-related gaps occur between the deflection plates and the outer shell of the heat exchanger. To be able to push the bundle of tubes into the shell, a gap having a width of a few millimeters (in general greater than 3 mm) is required. These gap losses inevitably lead to a reduction in the heat transferred.

Owing to the pressure differences between the individual segments, leakage flows inevitably occur through the gaps between shell and the deflection plates; the fluid flowing through the gap around the edge takes virtually no part in heat transfer. Overall, the leakage flows can be up to about 40% of the total flow through the space within the shell.

A specific type of reactor in which a special construction completely prevents the leakage flows occurring between the deflection plates and the shell in shell-and-tube apparatuses and the heat transfer is thus significantly improved is therefore used in a particularly preferred embodiment of the process of the invention.

The special construction comprises a further (sheet metal) shell, hereinafter referred to as sleeve, which is placed around the bundle of tubes. Unlike the actual shell, this sleeve is placed against the deflection plate without leaving a gap and fixed in place there. The sleeve is joined without leaving a gap to the deflection plates and to the tube plate on the side of the shell-side fluid inlet. This generally requires that this sleeve consists of relatively small segments and the segments are fastened to the deflection plates. For manufacturing reasons, these segments are fastened, preferably welded or fastened in another way, not only to the deflection plates but also to one another. As a result of this method of manufacture, the bundle of tubes, which is generally quite long, does not have to be threaded into the sleeve, so that gaps can be entirely dispensed with.

In operation, the fluid flows through the space inside the shell only within the bundle of tubes enclosed by the sleeve. The sleeve is advantageously not fastened around the bundle of tubes beyond the last deflection plate, so that the fluid flowing through the space inside the shell encloses the sleeve on the side facing away from the bundle of tubes and thus effects pressure equilibrium. In this design, only the pressure difference resulting from the dynamic pressure drops within the bundle of tubes is applied to the sleeve construction. The sleeve construction described therefore does not bear pressure and can therefore be constructed in rather low wall thicknesses compared to the outer shell. A preferably thin-walled sheet metal construction is therefore selected for the sleeve. The use of thin-walled materials enables the manufacture to be significantly simplified and the laying of the metal sheet against the deflection plates is made substantially easier.

As an alternative, it is conceivable to weld the outer shell in the above-described way directly to the deflection plates. Compared to such a solution, the sleeve construction presented here offers a series of advantages which, in particular, significantly simplify manufacture. The apparatus then does not consist of a large number of pressure-bearing welding seams. In addition, the deflection plates can be kept unchanged and do not have to have increased wall thicknesses, etc. The bundle of tubes enclosed by the sleeve can as hitherto be pushed into the pressure-bearing shell. However, the gap dimensions can here be made virtually any size, as a result of which assembly is also simplified at this point.

The use of the double-wall construction presented here makes it possible to eliminate the leakage flows which otherwise occur between the deflection plates and the outer shell. The elimination of the leakage flow has a favourable effect on heat transfer within the reactor in a number of ways. The most important effect is the increase in the mass flow which follows the planned path between the deflection plates. This increase in the mass flow results in an increase in the flow velocity which leads directly to an improvement in heat transfer between fluid and tube. Furthermore, for a given heating power within a segment, the radial temperature gradients decrease significantly. This reduction in the temperature gradients along a segment results in a higher average temperature difference between shell side and tube side, so that an improvement in heat transfer can also be assumed from this fact.

In the dissociation of MTBE, the sleeve construction in combination with the tube reactor used has a positive effect on the reaction in two ways. The first positive effect is improved heat transfer in the apparatus, which leads to a more constant temperature profile along the tube axis. The reaction-related temperature decrease is therefore smaller than in the case of a comparable apparatus without such a sleeve construction. The second important effect is the increase in the mass flow through the individual segments of the space within the shell, as a result of which the radial temperature profile is reduced. This effect improves the product qualities.

Apart from shell-and-tube apparatuses, it is also possible to use plate reactors for carrying out the dissociation reactions. Plate reactors have a structure analogous to plate heat exchangers. The spacing of the plates between which the catalyst is located is preferably 10-80 mm.

Secondary reactions occur in the dissociation of MTBE. These can be attributed either to MTBE or the dissociation products isobutene and methanol.

The formation of dimethyl ether (DME) normally occurs in the dissociation of MTBE. Here, two molecules of methanol react to form DME and water. The process of the invention is preferably operated so that the DME selectivity of the reaction to form DME is less than 10%, preferably less than 4%. (DME selectivity=2×[mol of DME formed]/[mol of unreacted MTBE]).

A further secondary reaction is the formation of C8-hydrocarbons by dimerization of isobutene. These consist mainly of a mixture of 2,4,4-trimethyl-1-pentene and 2,4,4-trimethyl-2-pentene.

The formation of further by-products is observed to a generally significantly smaller extent. These include, for example, isobutane, isoprene and dimethoxymethane and also higher oligomers (C12-HCs, C16-HCs).

The secondary reactions also include most reactions which proceed in parallel and in which impurities from the reactor feed react. These encompass, for example, the dissociation of 2-methoxybutane present in the MTBE. 1-butene and 2-butenes can be formed from this by elimination of methanol. 1,3-butadiene can be formed in the dissociation from 3-methoxy-1-butene or 1-methoxy-2-butene present in the MTBE.

Process Step d): Isolation of Isobutene

In step d) of the process of the invention, the dissociation products (VI) from the reactor are separated by distillation to give a fraction (VII), which in each case contains more than 50% by mass of the amount of methanol, TBA and water present in the dissociation products (VI).

Table 2 shows the boiling points as pure materials at 0.5 MPa(abs) of components typically present in the reactor output. Apart from isobutene, further C4-hydrocarbons (1-butene, 2-butenes) and DME are present as low boilers. Isoprene and dimethoxymethane are examples of intermediate boilers having boiling points between that of MTBE and that of C4-hydrocarbons. The intermediate boilers are partly formed in the reaction or get into the dissociation as impurities in the feed. High boilers, i.e. components having a boiling point higher than that of MTBE, present are, for example, tert-butanol, diisobutene and 2-methoxybutane.

The figure given for the water content in Table 2 relates to a mode of operation of the reactor without additional addition of water to the stream (V). If additional water is added here, the content of water and of TBA in the reactor output typically increases.

TABLE 2

Boiling points as pure materials at 0.5 $MPa_{(abs)}$, of components typically present in the reactor output, typical composition

| Pure material | Boiling point [° C.] | Typical proportion |
|---|---|---|
| Dimethyl ether | 19.2 | 0.1-2.5% by mass |
| Isobutene | 42.7 | 48-65% by mass |
| 1-Butene | 43.4 | 10-350 ppm by mass |
| 1,3-Butadiene | 45.1 | 0-50 ppm by mass |
| trans-2-Butene | 51.4 | 20-750 ppm by mass |
| cis-2-Butene | 54.1 | (Total 2-butenes) |
| 2-Butenes | 51.4 | 20-850 ppm by mass |
| Isoprene | 90.4 | 0-100 ppm by mass |
| Dimethoxymethane | 95.9 | 0-150 ppm by mass |
| Methanol | 111.5 | 27-37% by mass |

TABLE 2-continued

Boiling points as pure materials at 0.5 $MPa_{(abs)}$, of components typically present in the reactor output, typical composition

| Pure material | Boiling point [° C.] | Typical proportion |
|---|---|---|
| MTBE | 113.8 | 3-25% by mass |
| 2-Methoxybutane | 120.8 | 50-1700 ppm by mass |
| tert-Butanol | 131.3 | 0-2500 ppm |
| Water | 151.8 | 0.1-2% by mass |
| Diisobutene | 171.2 | 100-1500 ppm by mass |

In a preferred embodiment AFF5, the fractional distillation of the dissociation products (VI) is carried out in precisely one distillation column. This distillation column preferably has from 20 to 55 theoretical plates, more preferably from 25 to 45 theoretical plates and particularly preferably from 30 to 40 theoretical plates. The reflux ratio is, depending on the number of theoretical plates realized, the composition of the reactor output and the required purities of distillate and bottom product, preferably less than 5, more preferably less than 1. The operating pressure of the column can preferably be set in the range from 0.1 to 2.0 $MPa_{(abs)}$. It is advantageous to operate the column at a pressure lower than the pressure at which the dissociation reactor is operated. The dissociation products (VI) can then be transferred in gaseous form or partly in gaseous form after partial condensation to the distillation column. A compressor for increasing the pressure or a total condensation can thus be dispensed with.

Particular preference is given to transferring the reaction products (VI) to the distillation column after partial condensation. Here, preference is given to 30-70% by mass, particularly preferably 40-70% by mass, of the gas stream being condensed. The uncondensed gas stream is introduced directly into the column, and the condensed stream is introduced in the column after, if necessary, increasing the pressure by means of a pump. The heat liberated during cooling and partial condensation can be utilized for heat integration within the process or with other process parts. This heat integration can be carried out according to known standards of engineering, for example, by means of bottom vaporizers or preheaters or pre-vaporization in the feed to the column.

The gas phase and the liquid phase can be fed in at the same point or at different points on the column. The liquid phase is preferably fed in on the same plate or from one to five plates below that at which the gas phase is fed in.

The energy liberated in the partial condensation of the gas phase is preferably utilized at another point in the process, for example, for heating a column or for preheating the feed to the reactor.

To be able to condense isobutene against cooling water at the top of the column, a pressure of about 0.5 MPa(abs) is necessary. If the dissociation is operated, for example, at a pressure of 0.65 MPa(abs), it can be advantageous for the distillation column to be operated at an operating pressure of from 0.55 to 0.6 MPa(abs). The vaporizer of the column can be heated using, for example 0.4 MPa steam.

The fraction (VII) containing in each case more than 50% by mass of the amount of methanol, TBA and water present in the dissociation products (VI) is obtained as bottom product. In the case of a work-up corresponding to this embodiment AFF5, the fraction (VII) additionally contains MTBE. The fraction (VII) obtained according to AFF5, preferably contains more than 90% by mass of the amount of methanol present in the dissociation products (VI), more than 98% by mass of the amount of TBA present in the dissociation products (VI), more than 85% by mass of the amount of water present in the dissociation products (VI) and more than 98% by mass of the amount of MTBE present in the dissociation products (VI). The fraction separated off in this way particularly preferably contains virtually the total amount of the amount of MTBE, TBA, 2-methoxybutane and diisobutene present in the dissociation products (VI).

The intermediate boilers present in the output from the dissociation are preferably likewise separated off with the fraction (VII) obtained in this way, preferably to an extent of from 60 to 100% by mass, particularly preferably from 80 to 98% by mass.

The typical composition of the stream (VII) is obtained simply in combination with the concentration ranges given in Table 2.

At the top of the column, the fraction (XVII) containing mainly isobutene, methanol (owing to azeotrope formation with C4-hydrocarbons) and DME is obtained. 1-Butene, 2-butenes, 1,3-butadiene and intermediate boilers such as isoprene and dimethoxymethane can be present in traces. The total content of intermediate boilers is preferably below 50 ppm, the content of isoprene is particularly preferably below 20 ppm, and that of the dimethoxymethane is particularly preferably below 30 ppm.

The methanol content of the distillate is typically from 2 to 4% by mass. Based on the distillate stream calculated on a methanol-free basis, the concentration of isoprene is preferably less than 25 ppm, more preferably less than 1 ppm, the content of dimethoxymethane is preferably less than 10 ppm, more preferably 1 ppm, and the content of MTBE is preferably less than 5 ppm, more preferably less than 0.1 ppm.

In a further preferred embodiment AFF6, a first distillation analogous to that in AFF5 is carried out but the bottom product from the distillation is purified further in a second distillation. This gives an overhead fraction containing mainly MTBE and methanol. In addition, an essentially MTBE-free, methanol-rich bottom fraction in which the major part of the TBA and of the water is also present is obtained. When the column is operated without an additional side offtake, the C8-hydrocarbons are likewise constituents of the bottom fraction. However, it is possible to discharge at least part of the C8-hydrocarbons via a side offtake on the column. Such a process is described, for example, in DE 10 2006 040434. The bottom fraction is then fed as fraction (VII) to step e) of the process of the invention.

This second distillation column preferably has from 20 to 75 theoretical plates, more preferably from 30 to 65 and particularly preferably from 35 to 50. It can be advantageous for the column to be operated, depending on the number of theoretical plates realized and the MTBE conversion achieved in the dissociation reactor, at a reflux ratio of less than 10, preferably from 0.5 to 5. The operating pressure of the column is preferably set to a value in the range from 0.05 to 1 MPa(abs), more preferably from 0.1 to 0.3 MPa(abs). The column can be heated using, for example 0.4 MPa(abs) steam. The condensation can, depending on the operating pressure selected, be carried out against cooling brine, cooling water or air.

The fraction (VII) obtained in this way at the bottom preferably contains more than 95% by mass, particularly preferably more than 97% by mass, of methanol. The TBA content of the bottom product is preferably in the range from 100 to 1000 ppm by mass and the water content is preferably from 0.3 to 2.0% by mass. The intermediate boilers formed in the reaction section, e.g. isoprene and dimethoxymethane, are preferably present in an amount of less than 200 ppm, more preferably less than 100 ppm and particularly preferably less than 50 ppm.

The overhead fraction containing mainly MTBE and methanol contains methanol and the intermediate boilers formed in the reaction section, for example, isoprene and/or dimethoxymethane, in addition to the main constituent MTBE. This stream is preferably fed entirely or partly to step b) of the process of the invention. It is particularly preferably fed, in combination with embodiment AFF4 of the process step, into the middle column of the three columns, with the intermediate boilers being concomitantly separated off as overhead product in this column.

Process Step e): Removal of Water

In process step e), water is separated off from the fraction (VII) obtained in process step d) to give a fraction (VIII). In principle, the removal of water can be carried out by all industrially useable processes such as permeation, pervaporation, adsorption (for example pressure swing adsorption on molecular sieves) or distillation. The removal of water is preferably carried out by distillation in one or two distillation columns.

In a preferred embodiment AFF7, the water is separated off by distillation in a single distillation column. In this case, water is obtained at the bottom of the column, and all other components are obtained at the top of the column.

The distillation column preferably has from 15 to 50 theoretical plates, more preferably from 15 to 40 and particularly preferably from 20 to 35. It can be advantageous for the column to be operated, depending on the number of theoretical plates realized and the MTBE conversion achieved in the dissociation reactor, at a reflux ratio of less than 2, preferably from 0.5 to 1. The operating pressure of the column is preferably set to a value in the range from 0.05 to 1.0 MPa(abs), preferably from 0.1 to 0.5 MPa(abs). The column can be heated using, for example, 0.4 MPa steam. The condensation can, depending on the operating pressure selected, be carried out against cooling brine, cooling water or air.

In a further preferred embodiment AFF8, the removal of the water is carried out in two distillation columns which are operated as a dual-pressure distillation. Here, for example, the first column is operated at a lower pressure than the second column and the bottom of the first column is heated by means of the heat of condensation of the overhead vapours from the second column. The first of the two distillation columns preferably has from 5 to 35 theoretical plates, more preferably from 10 to 20 and particularly preferably from 15 to 25. The reflux ratio is from 0.1 to 2, preferably from 0.5 to 1. The operating pressure of the first column is preferably set to a value in the range from 0.01 to 1.0 MPa(abs), more preferably from 0.05 to 0.2 MPa(abs). The condensation can, depending on the operating pressure selected, be carried out against cooling brine, cooling water or air. The second of the two distillation columns preferably has from 10 to 45 theoretical plates, more preferably from 18 to 38 and particularly preferably from 20 to 30. The reflux ratio is from 1.0 to 5.0, preferably from 1.4 to 2.8. The difference between the pressure at the bottom of the first column and the pressure at the top of the second column determines the driving temperature difference in the vaporizer of the first column (=condenser of the second column). The operating pressure of the second column is preferably set to a value in the range from 0.05 to 0.5 MPa(abs) above the pressure at the bottom of the first column, more preferably from 0.15 to 0.25 MPa(abs) above. Heating of the two columns can be carried out using, for example, steam. It may be useful, in order to achieve better regulation of the column system, to equip the first column with an additional vaporizer operated using, for example, steam and the second column with an additional condenser which is, depending on the operating pressure selected, operated using, for example, cooling brine, cooling water or air.

As an alternative to heating the one or two drying columns by means of steam, heat integration with other process streams, for example the dissociation gases from the reactor, can be carried out. The heat integrations are carried out according to the known prior art, for example, via bottom vaporizers or preheaters or pre-vaporization of the feed to the column.

When the removal of water is configured as one distillation column, the distillate stream is obtained as fraction (VIII), while in the case of the configuration as two distillation columns, the sum of the two distillate streams obtained is obtained as fraction (VIII). Main constituents of the fraction (VIII) are methanol and MTBE, and the water content of the fraction (VIII) is less than 1% by mass, preferably less than 0.5% by mass, particularly preferably less than 0.1% by mass. The fraction (VIII) obtained is recirculated entirely or partly to step a) of the process of the invention.

The bottom stream (XLI) from the column or from the second column consists predominantly of water with traces of methanol and possibly further organic components. The water content is preferably greater than 99.9% by mass, more preferably greater than 99.99% by mass and particularly preferably greater than 99.999% by mass. This stream can either be utilized as process water, e.g. in one of the extraction steps present in the process, or be discharged as wastewater, if appropriate after further purification.

When acidic catalysts are used in process step c) the reactor output (VI) can have an acidic pH. This can result in inexpensive unalloyed steels not being able to be used in the subsequent process steps d) and e), in particular in the bottom region of the column and the two columns in process step d) and in the subsequent process step e), but higher-priced, high alloy steels having to be used instead in order to avoid corrosion caused by the acidic conditions. To avoid this, a stream of alkali can be introduced in process step d) or in process step e). In process step d), the alkali is preferably introduced into stream (VI), more preferably into the column or the first column at a point below the introduction of the feed. In process step e), the alkali is preferably introduced into stream (VII), more preferably into the column or the first column, below the point of introduction of the feed. The alkali is discharged from the process again with stream (XLI). There is therefore no risk of the alkali being recirculated to process step a) and here possibly leading to damage to the catalyst used.

As alkalis, it is possible to use aqueous solutions of alkali metal hydroxide or alkaline earth metal hydroxide. Preference is given to using sodium hydroxide and potassium hydroxide, in particular sodium hydroxide. The concentration of the hydroxides in the aqueous solution is from 0.5 to 30% by mass, in particular from 2 to 5% by mass. In the case of sodium hydroxide, the sodium hydroxide content is preferably in the range from 0.5 to 30% by mass, in particular in the range from 1 to 5% by mass, very particularly in the range from 2.5 to 3.5% by mass. The alkali is metered in such a way that a pH of preferably greater than or equal to 8, preferably from 8 to 12 is established in the bottom stream XLI.

Work-Up to Give High-Purity Isobutene

Commercial isobutene grades are usually virtually free of methanol. The isobutene stream obtained in the separation of the dissociation products (VI) by distillation still contains methanol. This can be removed by methods known per se, for example, by extraction. The extraction of methanol from the isobutene can be carried out, for example, using water or an aqueous solution as extractant, e.g. in an extraction column.

The extraction with water or an aqueous solution is preferably carried out in an extraction column which preferably has from 4 to 16 theoretical plates. The extractant preferably flows through the extraction column in countercurrent to the stream to be extracted. The extraction is preferably carried out at a temperature of from 15 to 50° C., more preferably from 25 to 40° C. For example, when an extraction column having more than 6 theoretical plates, and operating at a pressure of 0.9 MPa(abs) and a temperature of from 40° C. is used, a water-saturated isobutene having a methanol content of below 10 ppm can be obtained.

The methanol-containing water extract obtained in the extraction can be separated by distillation into water and methanol. The water can be recirculated as extractant to the extraction stage. The methanol is preferably recirculated to step a) of the process of the invention.

The moist isobutene stream from the extraction column can be worked up in one or more further distillation columns by removal of water and optionally DME to give dry isobutene. The dry isobutene is obtained as bottom product. In the condensation system at the top of the column, water in liquid form and DME with residual amounts of isobutene in liquid and/or gaseous form can be taken off after phase separation. A distillation column preferably used for drying preferably has from 30 to 80 theoretical plates, more preferably from 40 to 65 theoretical plates. The reflux ratio is, depending on the number of theoretical plates realized and the required purity of the isobutene, preferably less than 60, more preferably less than 40. The operating pressure of the column can preferably be set in the range from 0.1 to 2.0 MPa(abs). The DME-rich stream obtained at the top of the column can, if necessary, be separated further by distillation.

In addition, part of the DME can optionally be separated off from the stream VI as early as in the distillation in step d) by operating the condenser on the distillation column or reactive distillation column as a partial condenser. In this case, the C4 fraction present in the overhead product can be condensed and part of the gaseous dimethyl ether can be taken off as offgas stream.

A column for separating off DME and water having a decanter for separating off water present in the side stream from the column is particularly preferably used in the process of the invention. The integration of the decanter into the side stream of the column enables isobutene losses to be minimized. Such a process is also described, for example, in the patent application DE 102 38 370. The moist isobutene stream from the extraction is, if appropriate after removal of residual heterogeneous water, for example by means of a decanter or coalescer, fed into a column. DME is obtained at the top of the column and dry isobutene is obtained at the bottom. A side stream is taken off in liquid form from the column either below or above the point of introduction of the feed and is passed to a decanter. In the decanter, the aqueous phase is separated from the organic phase depleted in water. The water is discharged and the organic phase is recirculated to the column. The stream to the side decanter is preferably taken off below the point at which the feed is introduced into the column, and the recirculation of the stream from the decanter to the column is effected below the offtake point. The column preferably has from 30 to 80 theoretical plates, more preferably from 40 to 65 theoretical plates. The isobutene to be purified is preferably fed in above the 15th to 30th plate, in each case counted from the top. Preference is given to taking off all of the condensate of a theoretical plate from two to five theoretical plates above the feed point and feeding this into the decanter. After the water has been separated off, the organic phase is recirculated to the column at a point from one to two theoretical plates lower down.

The reflux ratio of the column is, depending on the number of theoretical plates realized and the required purity of the isobutene, preferably less than 60, more preferably less than 40. The operating pressure of the column is preferably in the range from 0.1 to 2.0 MPa(abs), particularly preferably in the range from 1.0 and 1.5 MPa(abs).

The isobutene obtained in this way can, for example, have the composition shown in Table 3.

TABLE 3

| Typical composition of commercial isobutene. Proportions by mass [kg/kg] | |
|---|---|
| C3-hydrocarbons | <0.000100 |
| Butanes | <0.001000 |
| Isobutene | >0.999000 |
| 1-Butene/2-butenes | <0.001000 |
| Methanol | <0.000030 |
| C5-hydrocarbons | <0.000500 |
| Water | <0.000050 |
| Oxygenates | <0.000010 |

Oxygenates: For example DME, dimethoxymethane

It is not technical feasible to separate off the linear butenes (1-butene, 2-butenes) present in the isobutene from the latter. The linear butenes are formed, inter alia from the dissociation of 2-methoxybutane which can be present in the MTBE. The formation of the linear butenes can therefore be avoided by complete removal of 2-methoxybutane before the dissociation. However, in order to limit distillation costs it can be advantageous to permit a small concentration of 2-methoxybutane. This is possible, in particular, when a catalyst which decomposes MTBE more quickly than 2-methoxybutane is used in step c) of the process.

Depending on purity requirements, lower concentrations of the secondary components can also be achieved if required.

The work-up of the C4-hydrocarbons which have been separated off in step a) and in the purification of the fraction (XVII) by extraction with water or aqueous solutions produces methanol/water mixtures which are preferably separated into water and methanol by distillation. These two distillations are preferably carried out jointly in one distillation. If further water/methanol streams are obtained in the process, it can be advantageous for these also to be included in the separation. For example, it is possible to combine the removal of water according to step e) with these water/methanol distillations. Particular preference is given to the combination with a column which, when configured as a dual-pressure distillation, is operated at a higher pressure.

The isobutene prepared by the process of the invention can be used, for example, for the preparation of diisobutene, isobutene oligomers, polyisobutylene, butyl rubber, t-butylaromatics, methacrylic acid, methyl methacrylate, methallyl chloride, or methallylsulphonates. In particular, it can be advantageous to use both the methanol obtained in the dissociation and the isobutene for preparing methyl methacrylate. Such a process for preparing methyl methacrylate is described, for example in EP 1 254 887, which is expressly incorporated by reference.

The invention and some embodiments of the individual process steps will be illustrated with the aid of FIGS. 1 to 12, without the invention being restricted to these.

FIG. 1 shows the process with its individual process steps;

FIGS. 2 to 12 showing embodiments of the individual process steps.

FIG. 1 shows the individual process steps with the associated streams. The isobutene-containing C4-hydrocarbons (II), a methanol-containing stream (IX) and the methanol-containing fraction (VIII) are fed to process step [a]. The methanol (III) which is reacted with the isobutene (I) from stream (II) to form the MTBE- and TBA-containing reaction mixture (IV) is present in the streams (VIII) and (IX). Stream (IX) can, for example, contain fresh methanol, i.e. methanol which has not been recovered in the process of the invention, or methanol which has been recovered in the extraction of methanol-containing C4 streams with water and subsequent methanol/water separation.

In [b] the MTBE- and TBA-containing fraction (V) is separated off from the reaction mixture (IV). This gives a stream of C4-hydrocarbons (X) which still contains proportions of methanol as a second stream.

In [c], fraction (V) is dissociated into the dissociation products (VI) from which a fraction (VII) containing more than 50% by mass of the amount of methanol, TBA and water present in the dissociation products (VI) is separated off in [d]. In addition, a methanol-containing isobutene stream (XVII) and, if appropriate, an MTBE- and methanol-containing stream (XL) are obtained.

Finally, in [e], water (XLI) is separated off from fraction (VII) and the remaining stream (VIII) is recirculated to [a].

FIG. 2 shows a preferred embodiment of process step [a]. The isobutene-containing C4-hydrocarbons (II) are mixed with the methanol-containing streams (VIII) and (IX) and fed to a first reactor (R11). The reactor (R11) is operated as an adiabatic fixed-bed reactor with recirculation, while the two subsequent reactors (R12, R13) are operated in a single pass. The temperature is in each case regulated separately upstream of the reactors R12/R13. The reaction mixture (IV) is obtained from reactor (R13).

FIG. 3 shows an embodiment [b1] of process steps [b]. The reaction mixture (IV) is separated in the column T-21 into the MTBE- and TBA-containing fraction (V) which is taken off as a side offtake stream, a methanol-containing overhead fraction of C4-hydrocarbons (X) and a C8-enriched bottom fraction (XV). This configuration of the column T-21 corresponds to the above-described embodiment AFF1.

A preferred work-up of the overhead fraction (X) is additionally shown. The methanol is washed out of the methanol-containing C4-hydrocarbons (X) in countercurrent with water (XI) in an extraction column (E-21). The water/methanol mixture (XII) is separated by distillation in column T-24 into the bottom product water (XI) which is recirculated to the extraction and the overhead product methanol (XIV). The stream (XIV) is preferably used as substream of stream (IX) in step [a].

FIG. 4 shows an embodiment [b2] of process step [b]. The reaction mixture (IV) is separated in the column T-21 into an MTBE-, 2-methoxybutane-, C8- and TBA-containing bottom fraction (XVI) and a methanol-containing overhead fraction of C4-hydrocarbons (X).

The column T-21 is in this embodiment preferably operated as a reactive distillation column. The configuration of the column T-21 as a reactive distillation column corresponds to the above-described embodiment AFF2.

The bottom fraction (XVI) is fractionated further in a further distillation column T-23. The MTBE- and TBA-containing fraction (V) is obtained as overhead product, and C8-hydrocarbons and 2-methoxybutane are at least partly separated off as bottom product (XV). Owing to the difficult MTBE/2-methoxybutane separation, MTBE is generally also still present. The column T-23 is preferably carried out at a sufficiently high pressure for the fraction (V) to be taken off in gaseous form at the top of the column and, if appropriate, after further heating, be able to be passed directly to the dissociation reaction. The purification of the MTBE in column T-23 corresponds to the above-described embodiment AFF3. In addition, the option of additionally adding water to the stream (V) in order to moderate the catalyst is indicated. The overhead fraction (X) is worked up in a manner analogous to embodiment [b1].

FIG. 5 shows an embodiment [b3] of process step [b]. The reaction mixture (IV) is separated in the column T-21 into an MTBE-, 2-methoxybutane-, C8- and TBA-containing bottom fraction (XVI) and a methanol-containing overhead fraction of C4-hydrocarbons (X). The column T-21 is preferably operated as a reactive distillation column in this embodiment. The configuration of the column T-21 as a reactive distillation column once again corresponds to the above-described embodiment AFF2.

In column T-22, low and intermediate boilers (L), for example residual amounts of C4-hydrocarbons and C5-hydrocarbons, are separated off from the fraction (XVI) at the top. Thus, for example, all components having a boiling point below 50° C. at 0.1 MPa(abs) can be separated off via the distillate. The purification of the MTBE in the column T-22 corresponds to the above-described embodiment AFF4. The bottom product (XVIII) is then separated in the column T-23 into the MTBE- and TBA-containing fraction (V) obtained at the top and the bottom product (XV) which has a composition analogous to that in [b2]. The purification of the MTBE in the column T-23 once again corresponds to the above-described embodiment AFF3. Here too, the option of additionally adding water to the stream (V) in order to moderate the catalyst is also indicated.

The work-up of the overhead fraction (X) is carried out in a manner analogous to embodiment [b1].

The advantage of this embodiment [b3] is that residual C4-hydrocarbons and intermediate-boiling components present in (XVI) can be separated off in a simple way. Thus, they get neither into the MTBE dissociation reactor nor into the overhead fraction (X).

FIG. 6 shows an embodiment [b4] of process step [b]. The reaction mixture (IV) is separated in the column T-21 into the MTBE- and TBA-containing fraction (V), which is taken off as a side offtake stream and a C8-enriched bottom fraction (XV). A mixture of C4-hydrocarbons, methanol and possibly MTBE is obtained as overhead fraction (XIX). This mixture is fed to a reactor R-21 in which residual amounts of unreacted isobutene react further to form MTBE. A methanol-containing stream (XX) can additionally be introduced into the reactor. The reactor output (XXI) is subsequently separated in a column T-25 into a methanol-containing C4-fraction (X) and an MTBE-containing bottom fraction (XXII). This fraction is utilized separately or can be recirculated entirely or partly to step [a] of the process. The overhead fraction (X) is once again worked up in a manner analogous to embodiment [b1]. In this embodiment, it can be advantageous to configure the column T-25 as a reactive distillation.

The advantage of this embodiment is that the isobutene conversion in step [a] of the process can be smaller, as a result of which less 2-methoxybutane is formed. As a result, a column T-23 as is used in embodiments [b2] and [b3] may be able to be omitted entirely or the column can be made significantly smaller.

FIG. 7 shows an embodiment [b5] of process step [b]. Here, purification to give high-purity 1-butene is carried out, with residual amounts of isobutene being converted into MTBE in the 1-butene purification.

The reaction mixture (IV) is separated in the column T-21 into the MTBE- and TBA-containing fraction (V), which is taken off as a side offtake stream and a C8-enriched bottom fraction (XV). A methanol-containing C4-fraction (XXIII) which still contains residual amounts of isobutene is taken off as overhead fraction (XXIII). The methanol is washed out of the stream (XXIII) by means of water (XXXIV) in an extraction column E-21. Amounts of 1,3-butadiene still present in the resulting stream (XXIV) are converted into n-butenes in a selective hydrogenation SHP by means of hydrogen, and the output from the hydrogenation (XXV) is fed to the column T-27. In column T-27, the first separation of the C4-hydrocarbons occurs. 1-Butene, the residues of isobutene, isobutane and low boilers present, in particular DME from the MTBE synthesis, are obtained as overhead product (XXVII). n-Butane, 2-butenes and possibly residual amounts of 1-butene are taken off at the bottom of the column as stream (XXVI). Any water obtained in heterogeneous form in the overhead stream (XXVII) is separated off. The distillate is fed to a reaction stage R-22 in which the isobutene is reacted with methanol (XXVIII). Catalyst and reaction conditions correspond to those of process step a) of the process of the invention.

The mixture (XXIX) obtained from the reaction is separated in the column T-28 into methanol-containing C4-hydrocarbons (XXX) and an MTBE-containing bottom fraction (XXXI). The MTBE-fraction preferably still contains methanol and is recirculated as substream of (IX) to step a) of the process of the invention.

Methanol is washed out of the stream (XXX) by means of water (XXXIV) in the extraction E-22. The water/methanol streams (XXXIII) and (XXXII) from the two extractions are separated in a common column T-26 into water (XXXIV) and methanol (XXXV). The stream (XXXV) is preferably recirculated as substream of (IX) to step a) of the process of the invention.

The water-saturated stream (XXXVI) is distilled in a subsequent distillation T-29 to give high-purity 1-butene (XXXVIII). It is obtained as bottom product from the column.

At the top of the column, isobutane and low boilers such as DME are obtained (XXXVII). To separate off the water, it is useful to equip the column T-29 with an overhead decanter in which the water separates out as second phase and can be discharged.

FIG. 8 shows an embodiment [d1] of process step [d]. The fractionation of the dissociation products (VI) which have preferably been partially condensed by heat integration with other process streams is carried out in a single distillation column T-41 in which the fraction (VII) containing methanol and unreacted MTBE as main constituents is obtained at the bottom. The overhead product (XVII) comprises isobutene, methanol and low boilers such as DME. Intermediate boilers such as C5-hydrocarbons, isoprene and dimethoxymethane are preferably obtained together with the bottom product. The isolation of isobutene in the column T-41 corresponds to the above-described embodiment AFF5.

FIG. 9 shows an embodiment [d2] of process step [d]. Here, the fractionation of the dissociation products (VI) is carried out in two distillation steps. This corresponds to the above-described embodiment AFF 6. The overhead product from the column T-42 (XVII) comprises isobutene, methanol and low boilers such as DME. Intermediate boilers such as C5-hydrocarbons, isoprene and dimethoxymethane are preferably obtained together with the bottom product. The bottom stream from the column T-42 (XXXIX) is fed to a second column T-43. An azeotrope of methanol and MTBE (XL) is taken off at the top of the column. The fraction (VII) which contains methanol, TBA and water but is virtually free of MTBE is obtained as bottom stream.

The MTBE/methanol azeotrope (XL) can be recirculated entirely or partly to the process. Recirculation to step a) or b) of the process is preferred. Particular preference is given to recirculation to one of the columns T-21, T-22 or T-23 of the preferred embodiments [b1], [b2], [b3] or [b4], or recirculation to the reactor R-21 of the embodiment [b4].

FIG. 10 shows an embodiment [e1] of process step [e]. The removal of water from the fraction (VII) is carried out in only one distillation column T-51. Here, water is obtained as bottom product (XLI) and the fraction (VIII) depleted in water is obtained as overhead product. The removal of water in the column T-51 corresponds to the above-described embodiment AFF7.

FIG. 11 shows an embodiment [e2] of process step [e]. The removal of water from the fraction (VII) is carried out in two distillation columns which are operated as a dual-pressure distillation. This corresponds to the above-described embodiment AFF8. In the first column T-52, which is operated under a lower pressure, the first substream of fraction (VIII) is obtained as overhead product. The bottom stream (XLII), which contains mainly methanol and water, is fractionated further in a second column which is operated under a higher pressure. Here, the second substream of the fraction (VIII) is obtained at the top and water (XLI) is obtained at the bottom. The column T-52 is preferably heated by the vapours from column T-53.

The configuration of process step e) in the form of a dual-pressure arrangement of two columns offers the advantage that it generally requires significantly less energy than the separation in only one column. Particular preference is given to a variant in which the feed to at least one of the columns is substantially vaporized using part of the heat of condensation of the dissociation gas from step c).

FIG. 12 shows a typical embodiment for the further workup of the methanol-containing isobutene stream (XVII) obtained in step [d].

Methanol is washed out of the stream (XVII) by means of water (XLIII) in an extraction E-71. The methanol-laden water (XLIV) is separated in the column T-72 into a methanol-containing stream (XLVI) and water (XLIII), and the water is recirculated to the extraction. Stream (XLVI) is preferably recirculated as substream of (IX) to step a) of the process of the invention.

The water-saturated isobutene stream (XLV), which still contains DME, is subsequently purified further in the column T-73. A DME-containing stream (XLVII) which normally still contains isobutene is obtained at the top of the column. To remove the water it is useful to equip the column T-29 with an overhead decanter in which the water separates out as second phase and can be discharged. At the bottom of the column isobutene (XLIX) is obtained.

Since the overhead stream from the column T-73 often still contains considerable amounts of isobutene, if can be useful to purify it in a further column (not shown). In this column, a DME stream depleted in isobutene is obtained at the top and an isobutene-enriched stream is obtained at the bottom. This bottom stream is preferably recirculated to the column T-73.

The procedure employed in the process of the invention for the synthesis and dissociation of MTBE can also be employed when using other alcohols. This applies in particular to the synthesis and dissociation of ethyl tert-butyl ether (use of ethanol as alcohol), n-propyl tert-butyl ether (use of n-propanol as alcohol), n-butyl tert-butyl ether (use of n-butanol as alcohol) and isobutyl tert-butyl ether (use of isobutanol as alcohol). In the case of all these alcohols, olefins can also be formed from them in the dissociation by elimination of water, which results in an additional introduction of water into the process.

EXAMPLES

The following examples illustrate the invention.

Example 1

Varying amounts of water were added to a mixture of synthetically produced raffinate I and methanol. The mixture was then introduced into a laboratory reactor. The reactor was a tube reactor (length 1000 mm, internal diameter 21 mm) with cooling jacket through which a heat transfer oil (Marlotherm SH from Sasol Olefins & Surfactants GmbH) flowed.

An acidic ion exchanger, viz. Amberlyst® 15 (Rohm & Haas), was used as catalyst. The catalyst used comprised pellets having an average diameter of 0.6-0.85 mm, a surface area of 45 m2/g and a bulk density of 770 g/l. The acid capacity of the catalyst, based on the moist catalyst, was 1.7 eq/ml.

The feed mixture was preheated to 36° C. in a heat exchanger before entering the reactor, and the jacket temperature was likewise set to 38° C. (temperature of the Marlotherm in the inlet to the reactor jacket) in all experiments. The pressure was set to a constant 1.2 MPa(abs) by means of a pressure regulator at the end of the reactor. The feed stream was regulated to 510 g/h, which at an amount of catalyst of 273.5 ml corresponds to an LHSV of 3.12 h$^{-1}$. The feed mixture entering the reactor and the product mixture leaving the reactor were analyzed by gas chromatography.

TABLE 4

Analyses of reactor feed, reactor output and isobutene conversion for Example 1.

|  |  | Experiment 1 | | Experiment 2 | | Experiment 3 | |
| --- | --- | --- | --- | --- | --- | --- | --- |
|  |  | Feed | Product | Feed | Product | Feed | Product |
| Isobutene | [M %] | 13.85 | 0.95 | 14.31 | 2.36 | 13.77 | 9.13 |
| Methanol | [M %] | 13.57 | 6.25 | 13.61 | 7.08 | 13.23 | 11.47 |
| MTBE | [M %] | 0.00 | 20.04 | 0.00 | 17.75 | 0.00 | 5.66 |
| TBA | [M %] | 0.00 | 0.02 | 0.00 | 0.26 | 0.00 | 1.40 |
| Butanes | [M %] | 12.23 | 12.15 | 12.30 | 12.32 | 12.21 | 12.20 |
| 1-Butene | [M %] | 36.56 | 36.53 | 36.20 | 36.59 | 37.14 | 36.93 |
| 2-Butenes | [M %] | 23.17 | 23.37 | 22.92 | 23.10 | 22.39 | 22.35 |
| Water | [M %] | 0.02 | 0.01 | 0.11 | 0.05 | 0.65 | 0.28 |
| Miscellaneous | [M %] | 0.60 | 0.67 | 0.55 | 0.49 | 0.61 | 0.58 |
| Isobutene conversion | [%] |  | 93.12 |  | 83.50 |  | 33.69 |

Table 4 shows the analyses of reactor feed, reactor output and also the calculated isobutene conversion. In Experiment 1, no additional water was mixed into the mixture of synthetically produced raffinate I; the water content of about 200 ppm results from the water originally present in the methanol and in the raffinate.

It can be seen that the isobutene conversion decreases significantly with the increasing water content; in Experiment 1, the conversion is about 93.1%, in Experiment 2 at about 1100 ppm of water in the feed only 83.5% and, finally, in Experiment 3 at about 6500 ppm of water in the reactor feed only about 33.7%. At the same time, the TBA formation increases with increasing water content; in Experiment 3, over one % by mass of TBA was measured in the reactor output.

Notes on Experiments 2 and 3:

In Examples 2 and 3 below, calculations were carried out using the steady-state simulation program ASPEN Plus (Version 2006.5 from AspenTech) to show the effects of the removal of water on the overall process.

To generate transparent, reproducible data, only generally available materials data were used. This simplification makes it possible for the calculations to be comprehended readily by a person skilled in the art. In the examples, the property method "UNIFAC-DMD" (see J. Gmehling, J. Li, and M. Schiller, Ind. Eng. Chem. Res. 32, (1993), pp. 178-193) was utilized.

For the modelling of the reactors R11, R12 and R13, the reactive distillation in the column T21 in the MTBE synthesis and the dissociation reactor in the MTBE dissociation, kinetic reactor models based on comprehensive experimental data using the respective catalysts were used in the calculations. For this reason, the reaction temperatures assumed in the modelling of the reactor are also reported in the examples. Since the composition of the inflowing and outflowing streams of the reaction stages is also indicated in each case, a person skilled in the art can reproduce the example by the remodelling of the reactors with prescribed conversions without knowing the precise equations for the kinetics.

Example 2

According to the Invention

Example 2 corresponds to the process shown in FIG. 1, assuming a variant [a1] as per FIG. 2 for the reaction of the isobutene, a variant [b3] as per FIG. 5, for the MTBE distillation, a variant [d1] as per FIG. 8 for the purification of the dissociation products and finally a variant [e1] as per FIG. 10 for the drying.

A C4-hydrocarbon stream (II) of 10 000 kg/h having the composition shown in Table 5 (typical raffinate I, cf. Table 1) is assumed as feed to the plant as per FIG. 1 or 2. The compositions of the fresh methanol introduced and of the recycle stream (VIII) coming from process step [e] are likewise shown in Table 5. The amount of fresh methanol was set so that a molar ratio of methanol to isobutene in the feed to the first reactor of 1.14 is obtained.

TABLE 5

Composition of the feed stream (II), the fresh methanol (IX) and the recycle stream (VIII) for Example 2.

|  | Raffinate I (II) | fresh methanol (IX) | Recycle stream (VIII) |
| --- | --- | --- | --- |
| Mass flow [kg/h] | 10000.0 | 502.8 | 2109.4 |
| Proportions by mass [kg/kg] |  |  |  |
| Dimethyl ether |  |  | 0.000025 |
| Isobutane | 0.025000 |  |  |
| Isobutene | 0.350000 |  | 0.000203 |
| 1-Butene | 0.340000 |  |  |
| 1,3-Butadiene | 0.001500 |  |  |
| n-Butane | 0.080000 |  |  |
| 2-Butenes | 0.202850 |  | 0.000001 |
| C5-hydrocarbons | 0.000150 |  | 0.001300 |
| MTBE |  |  | 0.147283 |
| 2-Methoxybutane |  |  | 0.004743 |
| Methanol |  | 0.997500 | 0.841886 |
| tert-Butanol |  |  | 0.001342 |
| Water | 0.000500 | 0.000250 | 0.000800 |
| Diisobutene |  |  | 0.002416 |

The C4-hydrocarbon stream (II), the fresh methanol (IX) and the methanol-containing recycle stream (VIII) are mixed and fed to the reactors R-11, R-12 and R-13 in variant [a1] as per FIG. 2.

The isobutene present in stream (II) is reacted in three adiabatic fixed-bed reactors connected in series, with the first reactor being configured as a circulation reactor, as shown in FIG. 2. Filling of the reactors with Amberlyst® 15 (Rohm & Haas) is assumed. The reactor R-11 is modelled with a volume of 18 $m^3$, R-12 with 10 $m^3$ and R-13 with 5 $m^3$. The entry temperature into the reactor R-11 is 40° C., and the assumed recirculation is 28 300 kg/h. The entry temperature into the reactor R-12 is 40° C., and the entry temperature into the reactor R-13 is 35° C. Under these conditions, a conversion of isobutene over all three reactors of about 97.8% is obtained. As secondary reactions, the formation of TBA from isobutene and water, the dimerization of isobutene to diisobutene, the reaction of methanol to form DME and water and the formation of 2-methoxybutane from n-butenes are taken into account in the kinetic model used. This gives the composition shown in Table 6 for the reactor output (VI) (feed to the column T-21).

TABLE 6

Composition of the feed stream (IV), the distillate and the bottom product (XVI) from the column T-21 for Example 2.

|  | Feed to T-21 (IV) | Distillate from T-21 (X) | Bottom product from T-21 (XVI) |
|---|---|---|---|
| Mass flow [kg/h] | 12612.2 | 6714.1 | 5898.1 |
| Proportions by mass [kg/kg] | | | |
| Dimethyl ether | 0.000394 | 0.000888 | |
| Isobutane | 0.019822 | 0.037235 | |
| Isobutene | 0.006077 | 0.000169 | 0.000001 |
| 1-Butene | 0.269581 | 0.506313 | 0.000099 |
| 1,3-Butadiene | 0.001189 | 0.002233 | 0.000001 |
| n-Butane | 0.063431 | 0.119125 | 0.000032 |
| 2-Butenes | 0.160274 | 0.299307 | 0.000844 |
| C5-hydrocarbons | 0.000336 | | 0.000719 |
| MTBE | 0.447633 | | 0.976586 |
| 2-Methoxybutane | 0.001678 | | 0.005414 |
| Methanol | 0.025947 | 0.034285 | 0.008509 |
| tert-Butanol | 0.002298 | | 0.005518 |
| Water | 0.000278 | 0.000445 | 0.000007 |
| Diisobutene | 0.001061 | | 0.002269 |

The variant [b3] as per FIG. 5 is assumed for the MTBE distillation. Accordingly the reactor output (IV) is fed to the column T-21. The column is configured as a reactive distillation. The column has, including the catalyst zone, 75 theoretical plates, the catalyst zone is located on plate 15 to plate 50 and the feed is introduced above plate 60, counted from the top. The catalyst volume is 0.2 $m^3$ per plate, with a KataMax® packing (Koch-Glitsch), filled with Amberlyst® 15 (Rohm & Haas) being assumed. The column is operated at a reflux ratio of 0.9 and a pressure of 0.6 MPa(abs). The temperature at the top is 51.4° C., the temperature at the bottom is 120.9° C. Under these boundary conditions, the conversion of isobutene in the reactive distillation column is 98%.

The bottom product (XVI) consists predominantly of MTBE (about 98% by mass) and meets commercial specifications for fuel-grade MTBE. In particular, the TBA content is less than 1% by mass, see Table 6. The distillate (X) consists predominantly of C4-hydrocarbons and also methanol, DME formed in the MTBE synthesis and water. The methanol can be removed by extraction with water, as shown in FIG. 5. The methanol-free C4-hydrocarbons (XIII) obtained from the extraction can be worked up by known methods to give high-purity 1-butene. In this context, it is important that the isobutene content, based on the 1-butene content, of stream (X) is less than 350 ppm. A high-purity 1-butene which meets commercial isobutene specifications (e.g. <2000 ppm of isobutene in the 1-butene) can therefore be obtained by means of a purely distillative process after removal or reaction of butadiene in a selective hydrogenation.

TABLE 7

Composition of the distillate (L) and the bottom product (XVIII) from the column T-22 and of the bottom product (XV) from the column T-23 for Example 2.

|  | Distillate from T-22 (L) | Bottom product from T-22 (XVIII) | Distillate from T-23 (V) | Bottom product from T-23 (XV) |
|---|---|---|---|---|
| Mass flow [kg/h] | 6.7 | 5891.4 | 5747.4 | 143.9 |
| Proportions by mass [kg/kg] | | | | |
| Dimethyl ether | | | | |
| Isobutane | 0.000158 | | | |
| Isobutene | 0.001252 | | | |
| 1-Butene | 0.086129 | 0.000001 | 0.000001 | |
| 1,3-Butadiene | 0.000712 | | | |
| n-Butane | 0.028309 | | | |
| 2-Butenes | 0.677852 | 0.000071 | 0.000073 | |
| C5-hydrocarbons | 0.036666 | 0.000678 | 0.000695 | |
| MTBE | 0.100000 | 0.977588 | 0.982811 | 0.769032 |
| 2-Methoxybutane | 0.000020 | 0.005420 | 0.002100 | 0.137986 |
| Methanol | 0.067130 | 0.008442 | 0.008653 | |
| tert-Butanol | | 0.005525 | 0.005662 | 0.000023 |
| Water | 0.001771 | 0.000005 | 0.000005 | |
| Diisobutene | | 0.002271 | | 0.092959 |

The MTBE stream (XVI) still contains a total of about 1700 ppm of C4- and C5-hydrocarbons. In the column T-22, these C4- and C5-hydrocarbons are removed from this stream to a residual content of 750 ppm by mass. The column has 52 theoretical plates and is operated at a reflux ratio of 212 and a pressure of 4.5 MPa(abs). The feed (XVI) is introduced above plate 22, counted from the top. The temperature at the top is 48.1° C. and the temperature at the bottom is 107.3° C.

The distillate from this column (L) has a residual content of 10% by mass of MTBE. The MTBE content could be reduced further by increasing the reflux ratio and/or the number of theoretical plates. Table 7 shows the composition of the distillate stream (L) and the bottom stream (XVIII) from column T-22.

The MTBE-stream (XVIII) which has been largely freed of low boilers is fed to the column T-23 in which primarily diisobutene and 2-methoxybutane are separated off at the bottom (XV). The column has 95 theoretical plates and is operated at a reflux ratio of 5.9 and a pressure of 0.95 MPa (abs). Stream (XVIII) is introduced above plate 28, counted from the top. The temperature at the top is 144.1° C., and the temperature at the bottom is 149.16° C. A gaseous fraction containing more than 98% by mass of MTBE is obtained as overhead product (V). The 2-methoxybutane content of the distillate was set to 2100 ppm by mass (see Table 7). The content of MTBE in the bottom product (XV) could be reduced by increasing the reflux ratio and/or the separation power. As a result of the operation of the column at elevated pressure, virtually the entire TBA present in the feed is distilled into the overhead product (V).

The MTBE-fraction (V) is, after further heating to the reaction temperature, fed as per FIG. 1 into the dissociation reactor in process step [c]. The dissociation reactor is modelled with a reactor volume of 5.5 m³, and filling with a catalyst which formally comprises magnesium oxide, aluminium oxide and silicon oxide and whose production is described in the patent DE 102006040432.7 is assumed.

The reactor is operated at 298° C. and 0.75 MPa(abs). Under these reaction conditions, an MTBE conversion of about 94% is obtained and the conversion of 2-methoxybutane is about 17%. Owing to the proportion of 2-methoxybutane being limited to 2100 ppm by mass in the reactor feed, a commercial specification for linear butenes in the isobutene product is not put at risk despite the dissociation of 2-methoxybutane into 2-butene. The reactor output contains water formed by DME formation and TBA dissociation, about 6000 ppm. The composition of the reactor output (IV) is shown in Table 8.

TABLE 8

Composition of the product (VI) from the dissociation reactor, the distillate stream (XVII) and the bottom stream (VII) from the column T-41 and also the bottom product (XLI) from the column T-51 for Example 2.

|  | Product from dissociation reactor (VI) | Distillate from T-41 (XVII) | Bottom product from T-41 (VII) | Bottom product from T-51 (XLI) |
|---|---|---|---|---|
| Mass flow [kg/h] | 5747.4 | 3610.3 | 2137.1 | 27.7 |
| Proportions by mass [kg/kg] | | | | |
| Dimethyl ether | 0.011201 | 0.017817 | 0.000025 | |
| Isobutane | | | | |
| Isobutene | 0.594182 | 0.945788 | 0.000200 | |
| 1-Butene | 0.000001 | 0.000001 | | |
| 1,3-Butadiene | | | | |
| n-Butane | | | | |
| 2-Butenes | 0.000301 | 0.000479 | 0.000001 | |
| C5-hydrocarbons | 0.000695 | 0.000347 | 0.001283 | |
| MTBE | 0.054055 | | 0.145371 | |
| 2-Methoxybutane | 0.001741 | | 0.004682 | |
| Methanol | 0.330802 | 0.034738 | 0.830956 | 0.000005 |
| tert-Butanol | 0.000493 | | 0.001325 | |
| Water | 0.005642 | 0.000829 | 0.013773 | 0.999995 |
| Diisobutene | 0.000887 | | 0.002385 | |

The variant [d1] as per FIG. 8 is assumed for the purification of the dissociation products. Accordingly, the reactor output (IV) is partially condensed and fed in two-phase form to the column T-41. The column has 42 theoretical plates and is operated at a reflux ratio of 0.3 and a pressure of 0.65 MPa(abs). The feed stream (VI) is introduced above plate 28, counted from the top. The temperature at the top is 50.8° C. and the temperature at the bottom is 117.0° C. The bottom product consists predominantly of unreacted MTBE (about 15% by mass) and methanol (about 83% by mass) and also the predominant part of the amount of water present in the feed stream (about 1.4% by mass), see Table 8.

The overhead product (XVII) is isobutene having a purity of greater than 94% by mass of isobutene. The limits for linear butenes (<1000 ppm by mass) and C5-hydrocarbons (<1000 ppm by mass) required in a typical isobutene specification are reliably achieved, see also Table 3. As shown in FIG. 12, the methanol can be removed if necessary by extraction with water. The residual water and the dimethyl ether can be separated off by means of a subsequent distillation and the isobutene (XLIX) can be concentrated to a purity of greater than 99.9% by mass.

The variant [e1] as per FIG. 10 is assumed for the drying of stream (VII). Accordingly, bottom stream (VII) of the column T-41 is fed to the column T-51. The column has 32 theoretical plates and is operated at a reflux ratio of 0.7 and a pressure of 0.11 MPa(abs). The feed stream (VII) is introduced above plate 14, counted from the top. The temperature at the top is 61.7° C. and the temperature at the bottom is 102.3° C.

The water is separated off from the distillate stream to a residual content of 800 ppm (see stream (VIII) in Table 5) and the distillate is recirculated to process step a). The bottom stream from the column consists of virtually pure water having a residual content of 5 ppm of methanol.

Example 3

Not According to the Invention

Example 3 serves as comparative example and does not comprise the process of the invention. Accordingly, a process as per FIG. 1 but without process step [e], i.e. the drying of the recycle stream (VII) and the corresponding removal of water, is modelled. The reaction of isobutene is carried out, in a manner analogous to Example 2, according to a variant [a1] as per FIG. 2, the MTBE distillation is carried out according to a variant [b3] as per FIG. 5 and the purification of the dissociation products is carried out according to a variant [d1] as per FIG. 8. The stream (VII) from process step [d] is recirculated to process step [a] in Example 3.

In a manner analogous to Example 2, a stream (II) of 10 000 kg/h is assumed as feed to the plant. The compositions of the stream (II), the fresh methanol introduced and the recycle stream (VII) coming from process step [d] are shown in Table 9. The compositions of stream (II) and stream (IX) are unchanged compared to Example 2, see Table 5. The amount of fresh methanol was again set so that a molar ratio of methanol to isobutene in the feed to the first reactor of 1.14 is obtained.

TABLE 9

Composition of the feed stream (II), the fresh methanol (IX) and the recycle stream (VII) for Example 3.

|  | Raffinate I (II) | Fresh methanol (IX) | Recycle stream (VII) |
|---|---|---|---|
| Mass flow [kg/h] | 10000.0 | 518.1 | 2109.1 |
| Proportions by mass [kg/kg] | | | |
| Dimethyl ether | | | 0.000056 |
| Isobutane | 0.025000 | | |
| Isobutene | 0.350000 | | 0.000200 |
| 1-Butene | 0.340000 | | |
| 1,3-Butadiene | 0.001500 | | |
| n-Butane | 0.080000 | | |
| 2-Butenes | 0.202850 | | 0.000001 |
| C5-hydrocarbons | 0.000150 | | 0.001097 |
| MTBE | | | 0.148802 |
| 2-Methoxybutane | | | 0.004200 |
| Methanol | | 0.997500 | 0.832828 |
| tert-Butanol | | | 0.000008 |
| Water | 0.000500 | 0.000250 | 0.010962 |
| Diisobutene | | | 0.001845 |

The C4-hydrocarbon stream (II), the fresh methanol (IX) and the methanol-containing recycle stream (VII) are mixed and fed to the reactors R-11, R-12 and R-13 in variant [a1] as per FIG. 2. The arrangement of the reactors, the reactor sizes and the entry temperatures are unchanged compared to Example 2.

The recycle stream (VII) contains about 1.1% by mass of water and thus significantly more water than in Example 2 (there stream (VIII)). As can be seen from Example 1, the conversion of isobutene into MTBE decreases at higher water concentrations under otherwise identical boundary conditions. Consequently, a conversion of isobutene over all three reactors of only 68.1% is obtained in Example 3 (97.8% in Example 2). The corresponding composition of the reactor output (IV) is shown in Table 10 (feed to the column T-21). Among other things, the TBA content in the reactor output (IV) is significantly higher at about 8000 ppm in Example 3 (about 2200 ppm in Example 2).

TABLE 10

Composition of the feed stream (IV), the distillate and the bottom product (XVI) from the column T-21 for Example 3.

| | Feed to T-21 (IV) | Distillate from T-21 (X) | Bottom product from T-21 (XVI) |
|---|---|---|---|
| Mass flow [kg/h] | 12627.2 | 7371.0 | 5256.2 |
| Proportions by mass [kg/kg] | | | |
| Dimethyl ether | 0.000659 | 0.001507 | |
| Isobutane | 0.019799 | 0.033916 | |
| Isobutene | 0.088515 | 0.080591 | 0.000016 |
| 1-Butene | 0.269260 | 0.461209 | 0.000077 |
| 1,3-Butadiene | 0.001188 | 0.002034 | 0.000001 |
| n-Butane | 0.063355 | 0.108517 | 0.000023 |
| 2-Butenes | 0.160304 | 0.273468 | 0.000777 |
| C5-hydrocarbons | 0.000302 | | 0.000726 |
| MTBE | 0.311137 | | 0.902868 |
| 2-Methoxybutane | 0.001238 | | 0.004278 |
| Methanol | 0.074873 | 0.038018 | 0.068855 |
| tert-Butanol | 0.008065 | | 0.020294 |
| Water | 0.000624 | 0.000739 | 0.000447 |
| Diisobutene | 0.000683 | | 0.001640 |

Once again, the variant [b3] as per FIG. 5 is assumed for the MTBE distillation, with the column T-21 being configured, as in Example 2, as a reactive distillation. Number of theoretical plates, catalyst volume, reflux ratio and column pressure remain unchanged compared to Example 2. The temperature at the top is 51.0° C., and the temperature at the bottom is 110.7° C. The conversion of isobutene in the reactive distillation column is about 47% under these boundary conditions.

The bottom product (XVI) consists predominantly of MTBE (about 90% by mass), methanol (about 7% by mass) and TBA (about 2% by mass). The stream therefore does not meet commercial specifications for fuel-grade MTBE (typical specification: TBA content of less than 1% by mass and methanol content of less than 1% by mass). The distillate (X) consists predominantly of C4-hydrocarbons and also methanol, DME formed in the MTBE synthesis and water. The methanol can be removed by extraction with water as shown in FIG. 5. Owing to the deterioration in the isobutene conversion as a result of the increased water content in the MTBE synthesis, the isobutene content, based on the 1-butene content, of stream (X) is about 17%. As a result, the methanol-free C4-hydrocarbons (XIII) after the extraction cannot be worked up directly by known methods to give high-purity 1-butene. High-purity 1-butene (typical specification: less than 2000 ppm of isobutene in the 1-butene) cannot be obtained by means of a purely distillative process after removal or reaction of butadiene in a selective hydrogenation. Reaction of the isobutene present in the 1-butene in a second MTBE stage (R-22 in FIG. 7) is also not possible since the isobutene content is, owing to the limitation imposed by the equilibrium, significantly too high in order to achieve the desired specification in simple fixed-bed reactors, if appropriate also with reactive distillation.

TABLE 11

Composition of the distillate (L) and the bottom product (XVIII) from the column T-22 and also the bottom product (XV) from the column T-23 for Example 3.

| | Distillate from T-22 (L) | Bottom product from T-22 (XVIII) | Distillate from T-23 (V) | Bottom product from T-23 (XV) |
|---|---|---|---|---|
| Mass flow [kg/h] | 5.5 | 5250.7 | 5028.8 | 221.9 |
| Proportions by mass [kg/kg] | | | | |
| Dimethyl ether | | | | |
| Isobutane | 0.000099 | | | |
| Isobutene | 0.015489 | | | |
| 1-Butene | 0.073655 | 0.000001 | 0.000001 | |
| 1,3-Butadiene | 0.000660 | | | |
| n-Butane | 0.021950 | | | |
| 2-Butenes | 0.673179 | 0.000076 | 0.000079 | |
| C5-hydrocarbons | 0.050616 | 0.000674 | 0.000703 | |
| MTBE | 0.100000 | 0.903705 | 0.924709 | 0.427689 |
| 2-Methoxybutane | 0.000017 | 0.004282 | 0.002100 | 0.053740 |
| Methanol | 0.047796 | 0.068876 | 0.071916 | |
| tert-Butanol | | 0.020315 | 0.000043 | 0.479732 |
| Water | 0.016538 | 0.000430 | 0.000449 | |
| Diisobutene | | 0.001641 | | 0.038839 |

The MTBE-stream (XVI) still contains a total of about 1600 ppm of C4- and C5-hydrocarbons. These C4- and C5-hydrocarbons are separated off from this stream to a residual content of 750 ppm by mass in the column T-22. The column is operated at a reflux ratio of 192, and number of theoretical plates and column pressure are unchanged compared to Example 2. The temperature at the top is 48.3° C., and the temperature at the bottom is 100.8° C. Table 11 shows the composition of the distillate stream (L) and the bottom stream (XVIII) from the column T-22.

The MTBE-stream (XVIII) which has been largely freed of low boilers is fed to the column T-23. In Example 3 the step according to the invention of water removal as per process step e) is absent. As a result, all of the water formed by TBA dissociation and DME formation in the ether dissociation is returned to the synthesis, more than 50% of it is there converted into TBA and thus, bound as TBA, returned to the dissociation. Without discharge of TBA, TBA or water would therefore continue to accumulate in the process and steady-state operation would not be possible. For this reason, not only diisobutene and 2-methoxybutane but also TBA are separated off at the bottom (XV) in the column T-23 in Example 3. The pressure in the column is therefore reduced by 0.2 MPa(abs) compared to Example 2; the number of theoretical plates remains unchanged. The column is operated at a reflux ratio of 2.6. The temperature at the top is 73.2° C., the temperature at the bottom is 87.6° C. Owing to the disappearance of the pressure azeotrope of MTBE and TBA at low pressures, TBA is discharged at the bottom in this mode of operation. The MTBE content of the bottoms was set so that, as in Example 2, 2% of the MTBE present in the feed stream (XVIII) is discharged at the bottom. A liquid fraction containing more than 92% by mass of MTBE and 8% by mass of methanol is obtained as overhead product (V). The 2-methoxybutane content of the distillate was, in Example 2 set to 2100 ppm by mass (see Table 11).

In contrast to Example 2, the MTBE-fraction (V) cannot, owing to the low pressure in the column T-23, be fed in gaseous form, without compression, to the dissociation reactor in process step [c]. In Example 3, the MTBE-fraction (V) is therefore taken off in liquid form from the column T-23, compressed to a pressure above the reaction pressure, vaporized completely and finally fed, after further heating, to the reaction temperature, to the dissociation reactor. The volume and the pressure of the dissociation reactor are unchanged compared to Example 2. The reactor is operated at 293° C. Under these reaction conditions, an MTBE conversion of about 93% is obtained, and the conversion of 2-methoxybutane is about 16%. The composition of the reactor output (IV) is shown in Table 12.

TABLE 12

Composition of the product (VI) from the dissociation reactor and the distillate stream (XVII) from the column T-41 for Example 3.

| | Product dissociation reactor (VI) | Distillate from T-41 (XVII) |
|---|---|---|
| Mass flow [kg/h] | 5028.8 | 2919.7 |
| Proportions by mass [kg/kg] | | |
| Dimethyl ether | 0.011522 | 0.019804 |
| Isobutane | | |
| Isobutene | 0.548113 | 0.943912 |
| 1-Butene | 0.000001 | 0.000001 |
| 1,3-Butadiene | | |
| n-Butane | | |
| 2-Butenes | 0.000294 | 0.000506 |
| C5-hydrocarbons | 0.000703 | 0.000419 |
| MTBE | 0.062409 | |
| 2-Methoxybutane | 0.001762 | |
| Methanol | 0.369455 | 0.034726 |
| tert-Butanol | 0.000003 | |
| Water | 0.004964 | 0.000631 |
| Diisobutene | 0.000774 | |

For the purification of the dissociation products, the variant [d1] as per FIG. 8 is assumed, as in Example 2. Number of theoretical plates, column pressure and reflux ratio of the column T-41 are unchanged compared to Example 2. The temperature at the top is 50.8° C., and the temperature at the bottom is 116.9° C. The bottom product (VII) consists predominantly of unreacted MTBE (about 15% by mass) and methanol (about 83% by mass) and also the predominant part of the amount of water present in the feed stream (about 1.1% by mass), see Table 9. Stream (VII) is recirculated directly to process step a) in Example 3.

Comparison of Example 2 (according to the invention) and Example 3 (not according to the invention) was able to show very clearly the advantages of the process of the invention. Due to the absence of process step e), the isobutene conversion is decreased very significantly in Example 3 owing to the increased proportion of water in the MTBE synthesis and the associated inhibition of the reaction, to such an extent that, under the same boundary conditions, neither in-specification 1-butene nor in-specification fuel-grade MTBE can be produced. Furthermore, the absence of process step e) makes discharge of TBA in process step b) necessary. This leads firstly to an increased isobutene loss caused by the isobutene bound in TBA and secondly to an increased energy consumption since, at the low pressure, offtake in gaseous form from the column T-23 and direct introduction into the dissociation reactor are no longer possible.

If steam is introduced in the ether dissociation in order to influence the reaction positively or alkali is introduced in the process steps after the ether dissociation in order to avoid corrosion, the disadvantages of a process without the removal of water according to the invention in process step e) are increased even further.

The invention claimed is:

1. A process for preparing isobutene, the process comprising:
    (a) reacting at least one hydrocarbon mixture comprising isobutene with at least one alcohol stream comprising methanol, over at least one acidic ion exchanger to give a first stream comprising methyl tert-butyl ether and tert-butanol;
    (b) separating the first stream by distillation to obtain a second stream comprising methyl tert-butyl ether and tert-butanol;
    (c) dissociating the second stream in the gas phase over a heterogeneous catalyst to give a third stream comprising isobutene, methanol, methyl tert-butyl ether, water and tert-butanol;
    (d) separating the third stream by distillation to give a fourth stream comprising more than 50% by mass of the amounts of methanol, tert-butanol, methyl tert-butyl ether and water present in the third stream and a fifth stream comprising isobutene;
    (e) separating the water from the fourth stream to less than 1% by mass by distillation to give a sixth stream comprising methanol, tert-butanol and methyl tert-butyl ether; and
    (f) totally or partially recirculating the sixth stream to the reacting (a) with the at least one hydrocarbon mixture.

2. The process of claim 1, wherein the separating (e) of the water from the fourth stream is carried out in two columns, with a first column being operated at a lower pressure and a bottom product therefrom being purified further in a second column operated at a higher pressure.

3. The process of claim 2, wherein the first column is at least partly heated by means of vapors from the second column.

4. The process of claim 2, wherein at least one additional water/methanol mixture is distilled in the second column.

5. The process of claim 2, further comprising adding water or water vapour to the second stream.

6. The process of claim 1, further comprising introducing a stream of alkali during the separating (d) of the third stream, during the separating (e) of the water from the fourth stream, or both during the separating (d) and the separating (e).

7. The process of claim 6, wherein the stream of alkali comprises an aqueous solution of an alkali metal hydroxide or an alkaline earth metal hydroxide.

8. The process of claim 6, wherein the alkali of the stream of alkali is removed during the separating (e) of the water from the fourth stream together with the water which is separated off.

9. The process of claim 6, wherein
    the separating (d) of the third stream employs one or two distillation columns, and
    the stream of alkali is introduced into a feed of the third stream to a first column of the one or two distillation columns.

10. The process of claim 7, wherein the separating (d) of the third stream employs one or two distillation columns, and the stream of alkali is introduced into a first column of the one or two distillation columns at a position below the point of introduction of a feed of the third stream.

11. The process of claim 7, wherein the separating (e) of the water from the fourth stream employs one or two distillation columns, and the stream of alkali is introduced into a feed of the third stream to a first column of the one or two distillation columns.

12. The process of claim 11, wherein the stream of alkali is introduced into a first column of the one or two distillation columns at a position below the point of introduction of the feed.

13. The process of claim 1, wherein a column, into which a reactor output is transferred, is operated at a lower pressure than a reactor.

14. The process of claim 13, wherein heat from cooling and partial condensation of the reactor output is integrated into the process.

15. The process of claim 1, wherein the only water present during the reacting (a) is a maximum amount of 400 ppm water present in the hydrocarbon mixture and less than 1% by mass of water present in the methanol.

16. The process of claim 1, wherein the only water recirculated to the reacting (a) is an amount of less than 1% by mass of the sixth stream.

17. The process of claim 1, wherein the separating (e) forms a sixth stream containing less than 0.5% by mass of water.

18. The process of claim 1, wherein the separating (e) forms a sixth stream having less than 0.1% by mass of water.

* * * * *